(12) United States Patent
Ramljak et al.

(10) Patent No.: US 7,371,776 B2
(45) Date of Patent: May 13, 2008

(54) METHODS AND COMPOSITIONS FOR TREATING CANCER

(75) Inventors: Danica Ramljak, McLean, VA (US); Leo J. Romanczyk, Jr., Hackettstown, NJ (US); Robert B. Dickson, Kensington, MD (US)

(73) Assignee: Mars, Incorporated, McLean, VA (US)

( * ) Notice: Subject to any disclaimer, the term of this patent is extended or adjusted under 35 U.S.C. 154(b) by 363 days.

(21) Appl. No.: 11/045,947

(22) Filed: Jan. 29, 2005

(65) Prior Publication Data

US 2005/0171029 A1 Aug. 4, 2005

Related U.S. Application Data

(60) Provisional application No. 60/540,641, filed on Jan. 30, 2004.

(51) Int. Cl.
*A61K 31/35* (2006.01)
(52) U.S. Cl. .............................................. 514/456.009
(58) Field of Classification Search ...................... None
See application file for complete search history.

(56) References Cited

U.S. PATENT DOCUMENTS 5,554,645 A 9/1996 Romanczyk, Jr. et al. .. 514/456
6,297,273 B1 10/2001 Romanczyk, Jr. ........... 514/456
6,670,390 B1 12/2003 Romanczyk, Jr. et al. .. 514/456

FOREIGN PATENT DOCUMENTS

| JP | 57-118580 | 7/1982 |
| JP | 2002/128685 | 10/2000 |
| WO | 2004/062654 A1 | 7/2004 |

OTHER PUBLICATIONS

West, et al., Activation of the P13K/Akt Pathway and Chemotherapeutic Resistance, *Drug Resistance Updates*, 5:234-248 (2002.
Pianetti, et al., Green Tea Polyphenol Epigallocatechin-3 Gallate Inhibits Her-2/Neu Signaling, Proliferation, and Transformed Phenotype of Breast Cancer Cells, *Cancer Res.* 62:652-655 (2002).
Dancy, et al., Issues and Progress With Protein Kinase Inhibitors for Cancer Treatment, *Nature Reviews*, 2:297-313 (Apr. 2003).
Stoner, et al., Polyphenols as Cancer Chemopreventative Agents, *J. Cellular Biochem. Supp 22*: 169-180 (1995).
Kozikowski, et al., Studies in Polyphenol Chemistry and Bioactivity, *J. Org. Chem. 68*:1641-1658 (2003).

*Primary Examiner*—L. E. Crane
(74) *Attorney, Agent, or Firm*—Nada Jain, P.C.

(57) ABSTRACT

This invention relates to methods of inducing dephosphorylation of a hyperphosphorylated cell cycle regulatory protein in a tumor cell in which hyperphosphorylation of said protein contributed to cell transformation, the method comprising contacting the tumor cell with a procyanidin oligomer of five monomeric units connected via a C-4→C-8 linkage. Examples of such compounds are [EC-(4β→8)]$_4$-EC, and [EC-(4β→8)]$_3$-EC-(4β→8)-C, wherein EC is epicatechin and C is catechin.

10 Claims, 3 Drawing Sheets

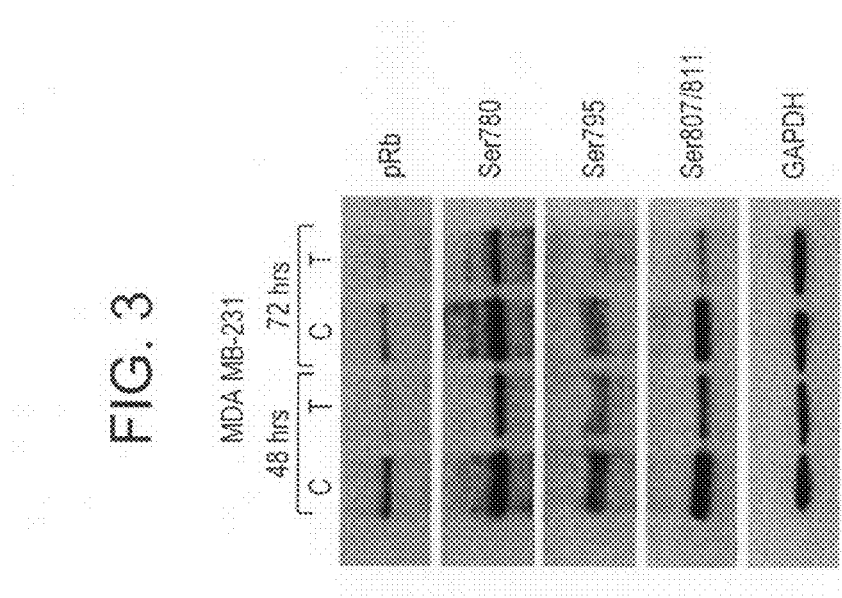

METHODS AND COMPOSITIONS FOR TREATING CANCER

This application claims the benefit, under 35 USC Section 119, of the U.S. Provisional Appl. No. 60/540,641 filed Jan. 30, 2004, the disclosure of which is hereby incorporated herein by reference.

FIELD OF THE INVENTION

This invention relates to compositions, and methods of use thereof, containing polyphenols such as procyanidins and derivatives thereof, for treating certain tumors, and more generally to inducing dephosphorylation of a hyperphosphorylated cell cycle regulatory protein in a tumor cell in which hyperphosphorylation of said protein contributed to cell transformation.

BACKGROUND OF THE INVENTION

The proanthocyanidins have attracted a great deal of attention in the fields of medicine and nutrition due to the wide range of their biological activities (e.g. U.S. Pat. No. 6,638,971). Applicants have now discovered specific anticancer properties of procyanidins and derivatives thereof and their effect on regulation of proteins involved in the regulation of the cell cycle. Examples of such proteins are Cdc2, AKT, forkhead transcription factor, p53 and pRb.

Cdc2 is a protein kinase which is important in the control of both cell cycle and apoptosis [Konishi, Y. et al., *Molec. Cell*, 9: 1005-1016, 2002]. Phosphorylation of Cdc2 Tyr15 residue is inhibitory to its function and causes resistance to paclitaxel (Taxol®)-induced apoptosis [Tan, M. et al., *Molec. Cell*, 9: 993-1004, 2002].

AKT, encoded by a known oncogene, also known as protein kinase B, is a serine/threonine kinase that plays a central role in promoting the survival of a wide range of cell types [Khwaja, A., *Nature*, pp. 33-34 (1990)]. Inhibition of AKT induces apoptosis of human ovarian cancer cells which demonstrates that AKT may be an important target for cancer treatment and other proliferative disorders [Zang, Q. Y., et al, *Oncogene*, 19 (2000)]. In fact, AKT is commonly used as a marker for ovarian and breast cancers. AKT promotes cell survival by phosphorylating forkhead transcription factor (FKHR) at amino acid position Ser256, which results in inhibition of FKHR function [Brunet, A., et al., *Cell*, 96:857-868 (1999)]. AKT-mediated phosphorylation of Ser256 of FKHR inhibits apoptosis through decreasing FKHR-controlled Fas ligand expression [Jackson, J. G. et al., *Oncogene*, 198: 4574-4581, 2000; Nakamura, N. et al., *Mol. Cell. Biol.*, 20: 8969-8982, 2000; Rena, G. et al., *EMBO J.*, 21: 2263-2271, 2002.]

Early genetic changes associated with malignancy involve genes that regulate cell cycle progression and often these changes result in a loss of $G_1$ checkpoint in tumor cells, due to defects in retinoblastoma (pRb) and p53 cell cycle pathways [Lomazzi, M. et al., *Nat Genet.*, 31:190-194, 2002]. Post-transcriptional modification of these proteins appears to be an important mechanism of their functional regulation.

For example, phosphorylation of Ser392 of p53 activates specific DNA binding functions by stabilizing p53 tetramer formation [Keller, D. M. et al., *Molec. Cell*, 7: 283-292, 2001; Fiscella, M., et al., *Oncogene*, 9:3249-3257, 1994]. Several stress stimuli are reported also to phosphorylate Ser392 (Ser389 in mouse). In addition, recent analysis of p53 phosphorylation in human tumors revealed that among 10 sites analyzed, hyperphosphorylation of residues Ser15, Ser 81, and Ser392 and acetylation were among the most frequent modifications [Minamoto, T. K., et al., *Oncogene*, 20: 3341-3347, 2001]. Increased phosphorylation of p53 at Ser392 in human tumors is frequent [Furihata, M. et al., *J. Pathol.*, 197: 82-88, 2002].

The serine residues of pRb are also critically involved in $G_1$/S transition. It is known that cyclin D-Cdk4 phosphorylates pRb at Ser780 and possibly Ser795 [Kitagawa, M., at al., *EMBO J.*, 15: 7060-7069, 1996; Panigone, S. et al., *Oncogene*, 19: 4035-4041, 2002]. Both transforming growth factor β (TGF-β) and retinoic acid have been reported to cause $G_1$ cell cycle arrest by dephosphorylating pRb at Ser780, Ser795 and Ser807/811 [Hu, X. et al., *Biochem. Biophys. Res. Commun.*, 276: 930-939, 2000; Dimbert, A. et al., *Blood*, 99: 2199-2206, 2002].

Thus, the cell cycle regulatory proteins are useful targets for tumor therapy. At present, there is a need in the art for compounds that can target hyperphosphorylation and/or overexpression of these proteins to prevent and/or treat proliferative growth. It has now been found that compounds of this invention and compositions thereof are effective for these uses.

SUMMARY OF THE INVENTION

The invention relates to compositions, products and methods for treatment of certain tumors, particularly certain cancers, and more generally to inducing dephosphorylation of hyperphosphorylated cell cycle regulatory proteins in tumor cells.

In one aspect, the invention relates to a composition, such as a pharmaceutical, a food, a food additive, or a dietary supplement comprising the compounds of the invention such as procyanidins or derivatives thereof. The composition may optionally contain an additional chemotherapeutic agent, or may be administered in combination with an additional chemotherapeutic agent. Packaged products containing the above-mentioned compositions and a label and/or instructions for use to treat tumors are also within the scope of the invention.

In another aspect, the invention relates to a method of inducing dephosphorylation of a hyperphosphorylated cell cycle regulatory protein, for example Cdc2, FKHR, p53 and pRb, in a tumor cell in which hyperphosphorylation of said protein contributed to transformation.

In yet another aspect, the invention relates to methods of treating a tumor, in which hyperphosphorylation of a cell cycle regulatory protein contributed to the tumor phenotype, by administering to a mammal, such as a human or a veterinary animal, an effective amount of a procyanidin or a derivative thereof. Generally, the invention relates to methods for treating tumors in a mammal, such as a human or a veterinary animal, by administering an effective amount of the compounds of the invention. Non-limiting examples of cancers are breast, ovarian, prostate, lung, colorectal and pancreatic cancer.

In a further aspect, the invention relates to a method comprising (i) profiling a subject for the overexpression and/or hyperphosphorylation status of cell cycle regulatory proteins, for example, Cdc2, AKT, FKHR, p53, cyclin D1 and pRb, and (ii) treating the subject exhibiting hyperphosphorylation and/or overexpression of these proteins by administering an effective amount of the compounds of the invention.

BRIEF DESCRIPTION OF THE DRAWINGS

FIG. 3 represents high resolution profiling of pRb (using LPS-immunoblotting technology) in human breast cancer cells treated with pentamer. To test for equality of loading blots were probed with GAPDH. The data are representative of two independent immunoblotting analysis using same protein samples.

DETAILED DESCRIPTION

Figure 1:
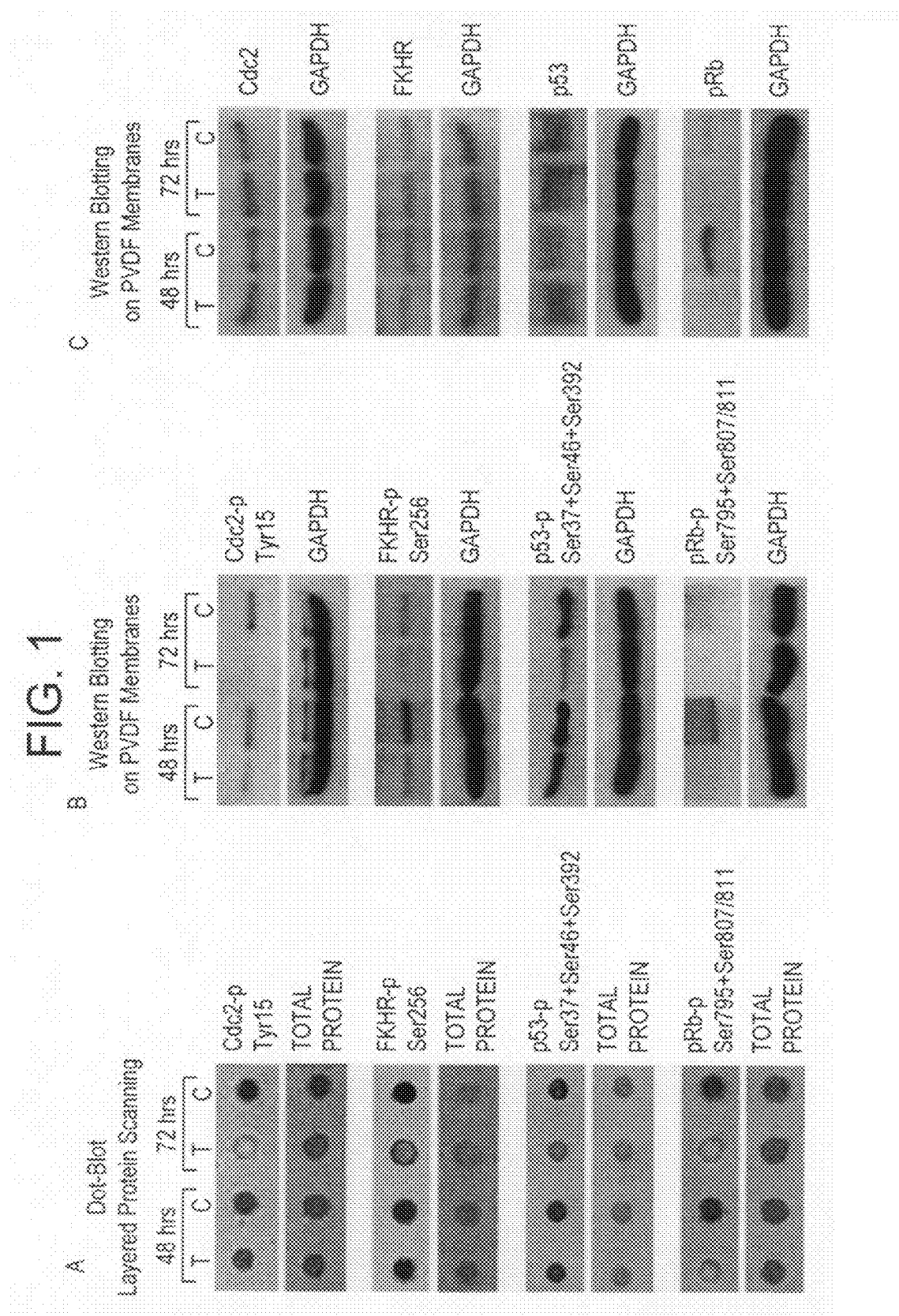
FIG. 1A-C represents results of LPS (layered protein scanning) multi-well plate and immunoblotting analysis of pentamer-treated human breast cancer cells. A) LPS dot blot of MDA MB-231 cells treated with 100 μg/mL of pentamer (T) for 48 and 72 hours and control cells treated with DMSO (C); B) Western Blot of the same samples as in A); C) Western Blot of reprobed membranes with antibodies detecting Cdc2, FKHR, p53, and pRb independently from their phosphorylation status. To test equality of loading, blots were reprobed with GAPDH. The results are representative of two independent immunoblotting analyses using the same protein samples.

All patents, patent applications and references cited in this application are hereby incorporated herein by reference. In case of any inconsistency, the present disclosure governs.

The present invention relates to a composition comprising an effective amount of the compound having the following formula $A_n$, or a pharmaceutically acceptable salt or derivative thereof (including oxidation products):

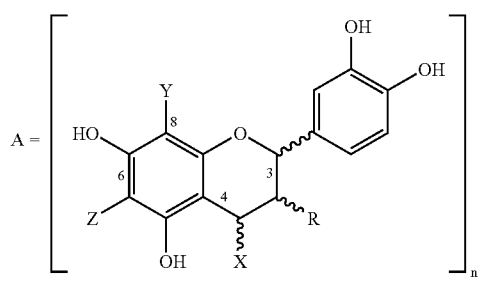

wherein
n is an integer from 2 to 18;
R and X each have either α or β stereochemistry;
R is OH, O-sugar or O-gallate;
the substituents of C-4, C-6 and C-8 are X, Z and Y, respectively, and bonding of monomeric units occurs at C-4, C-6 or C-8;

when any C-4, C-6 or C-8 are not bonded to another monomeric unit, X, Y and Z are hydrogen or a sugar; and the sugar is optionally substituted with a phenolic moiety at any position, for instance, via an ester bond.

Monomeric units in the above formula may be bonded via 4→6 and 4→8 linkages. The sugar can be selected from the group consisting of glucose, galactose, rhamnose, xylose, and arabinose. The sugar is preferably a monosaccharide or di-saccharide. The phenolic moiety is selected from the group consisting of caffeic, cinnamic, coumaric, ferulic, gallic, hydroxybenzoic and sinapic acids. Examples of derivatives include glycosides, gallates, esters, oxidation products of compound $A_n$ etc. Oxidation products may be prepared as disclosed in U.S. Pat. No. 5,554,645, the relevant portions of which are incorporated herein by reference.

In one embodiment, the composition comprises an effective amount the compound having the formula $A_n$, or a pharmaceutically acceptable salt or derivative thereof (including oxidation products):

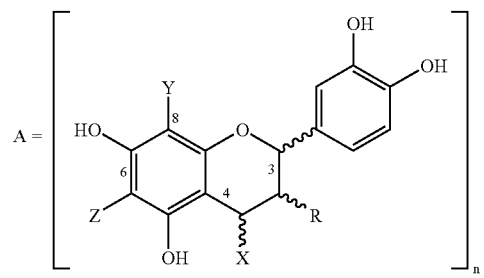

wherein
n is an integer from 2 to 18;
R and X each have either α or β stereochemistry;
R is OH;
the substituents of C-4, C-6 and C-8 are X, Z and Y, respectively, and bonding of monomeric units occurs at C-4, C-6 and C-8; and when any C-4, C-6 or C-8 are not bonded to another monomeric unit, X, Y and Z are hydrogen.

Monomeric units in the above formula may be bonded via 4→6 and 4→8 linkages. The sugar can be selected from the group consisting of glucose, galactose, rhamnose, xylose, and arabinose. The sugar is preferably a monosaccharide or di-saccharide. The phenolic moiety is selected from the group consisting of caffeic, cinnamic, coumaric, ferulic, gallic, hydroxybenzoic and sinapic acids. Examples of derivatives include glycosides, gallates, esters, oxidation products etc.

Examples of the compounds useful for products, and in the methods of the invention include the compounds wherein the integer n is 3 to 18; 2 to 12; 3 to 12; 2 to 5; 4 to 12; 5 to 12; 4 to 10; or 5 to 10. In some embodiments, the compound is a procyanidin tetramer or a pentamer.

In one embodiment the polymeric compound $A_n$ has the following formula:

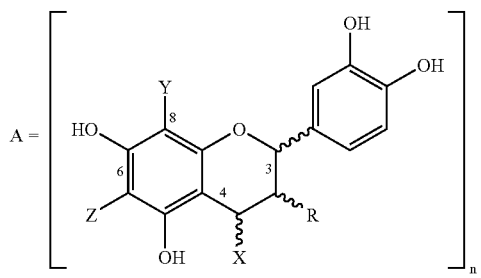

wherein
n is 5;
R and X each have either α or β stereochemistry;
R is OH, O-sugar or O-gallate;
the substituents of C-4, C-6 and C-8 are X, Z and Y, respectively, and bonding of monomeric units occurs at C-4, C-6 and C-8; and
when any C-4, C-6 or C-8 are not bonded to another monomeric unit, X, Y and Z are hydrogen or sugar;
the sugar is optionally substituted with a phenolic moiety at any position, for instance, via an ester bond.
or a pharmaceutically acceptable salt or derivative thereof (including oxidation products).

Monomeric units in the above formula may be bonded via 4→6 and 4→8 linkages. The sugar can be selected from the group consisting of glucose, galactose, rhamnose, xylose, and arabinose. The sugar is preferably a monosaccharide or a di-saccharide. The phenolic moiety is selected from the group consisting of caffeic, cinnamic, coumaric, ferulic, gallic, hydroxybenzoic and sinapic acids. Examples of derivatives include glycosides, gallates, esters, oxidation products etc.

In another embodiment the polymeric compound $A_n$ has the following formula:

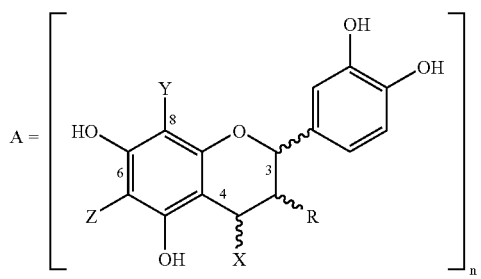

wherein
n is 5;
R and X each have either α or β stereochemistry;
R is OH;
the substituents of C-4, C-6 and C-8 are X, Z and Y, respectively, and bonding of monomeric units occurs at C-4, C-6 and C-8; and
when any C-4, C-6 or C-8 are not bonded to another monomeric unit, X, Y and Z are hydrogen;
or a pharmaceutically acceptable salts or derivative thereof (including oxidation products).

Monomeric units in the above formula may be bonded via 4→6 and 4→8 linkages. The sugar can be selected from the group consisting of glucose, galactose, rhamnose, xylose, and arabinose. The sugar is preferably a monosaccharide or di-saccharide. The phenolic moiety is selected from the group consisting of caffeic, cinnamic, coumaric, ferulic, gallic, hydroxybenzoic and sinapic acids. Examples of derivatives include glycosides, gallates, esters, oxidation products etc.

Examples of the pentamers may be: [EC-(4β→8)]$_4$-EC, [EC-(4β→8)]$_3$-EC-(4β→6)-EC, [EC-(4β→8)]$_3$-EC-(4β→8)-C, and [EC-(4β→8)]$_3$-EC-(4β→6)-C, wherein EC is epicatechin and C is catechin.

In one example, pentamer has the following formula:

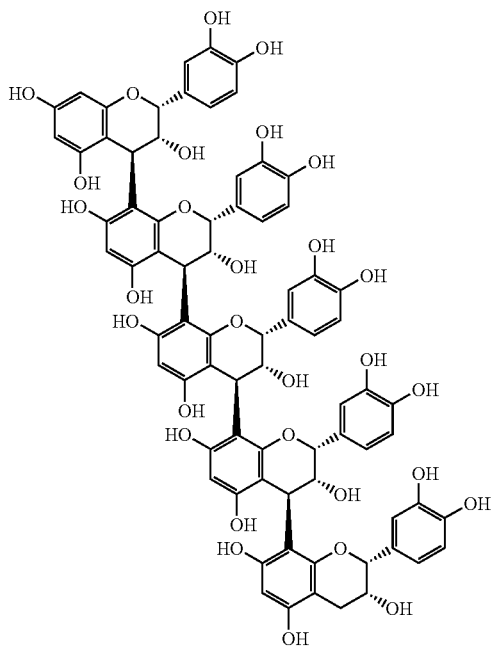

Both purified individual pentamers and pentamer mixtures may be used. The degree of purity may, for example, be at least about 50%, or at least about 60%, or at least about 70%, or at least about 80%, or at least about 90%, or at least about 92%, or at least about 95%, or at least about 98%, or at least about 99%. The above degrees of purities may be utilized for any compound of the formula $A_n$, its salts and derivatives.

Methods of Use

The invention relates to methods for treatment of certain tumors, particularly certain cancers, and more generally to inducing dephosphorylation of hyperphosphorylated cell cycle regulatory proteins in tumor cells. Non-limiting examples of cancers to be treated according to the methods described herein are breast, ovarian, prostate, lung, colorectal and pancreatic cancer. Any compound described in the application may be used to practice the methods described herein.

In certain embodiments the invention provides a method of inducing, promoting or stimulating dephosphorylation of a hyperphosphorylated cell cycle regulatory protein in a tumor cell, in which hyperphosphorylation of said protein contributed to transformation, comprising contacting the tumor cell with an effective amount of a compound having the formula $A_n$, or a pharmaceutically acceptable salt or derivative thereof (including oxidation products):

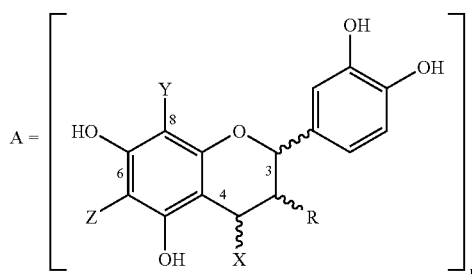

wherein n is an integer from 2 to 18;

R and X each have either α or β stereochemistry;

R is OH, O-sugar or O-gallate;

the substituents of C-4, C-6 and C-8 are X, Z and Y, respectively, and bonding of monomeric units occurs at C-4, C-6 or C-8;

when any C-4, C-6 or C-8 is not bonded to another monomeric unit, X, Y and Z are hydrogen or a sugar; and the sugar is optionally substituted with a phenolic moiety at any position, for instance, via an ester bond.

For example, the above method may involve use of a compound $A_n$, or a pharmaceutically acceptable salt or derivative thereof (including oxidation products), wherein R is OH, and when any C-4, C-6 or C-8 is not bonded to another monomeric unit, X, Y and Z are hydrogen. In some embodiments of the above method, the sugar in the formula $A_n$ is preferably a monosaccharide or di-saccharide. Examples of suitable sugars are glucose, galactose, rhamnose, xylose, and arabinose. Examples of phenolic moieties are as described above.

In one of the embodiments, the method of inducing, promoting or stimulating dephosphorylation of a hyperphosphorylated cell cycle regulatory protein in a tumor cell, in which hyperphosphorylation of said protein contributed to transformation, comprises contacting the tumor cell with an effective amount of a compound having the formula $A_n$, or a pharmaceutically acceptable salt or derivative thereof (including oxidation products):

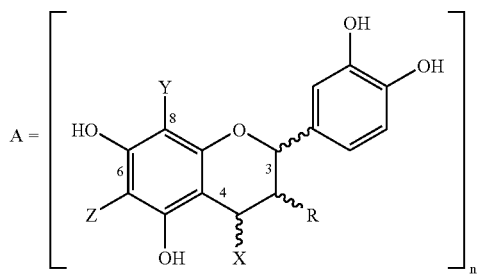

wherein n is 5;

R and X each have either α or β stereochemistry;

R is OH;

the substituents of C-4, C-6 and C-8 are X, Z and Y, respectively, and bonding of monomeric units occurs at C-4, C-6 and C-8; and when any C-4, C-6 or C-8 are not bonded to another monomeric unit, X, Y and Z are hydrogen.

Examples of the pentamers may be: [EC-(4β→8)]$_4$-EC, [EC-(4β→8)]$_3$-EC-(4β→6)-EC, [EC-(4β→8)]$_3$-EC-(4β→8)-C, and [EC-(4β→8)]$_3$-EC-(4β→6)-C, wherein EC is epicatechin and C is catechin.

In one example, pentamer has the following formula:

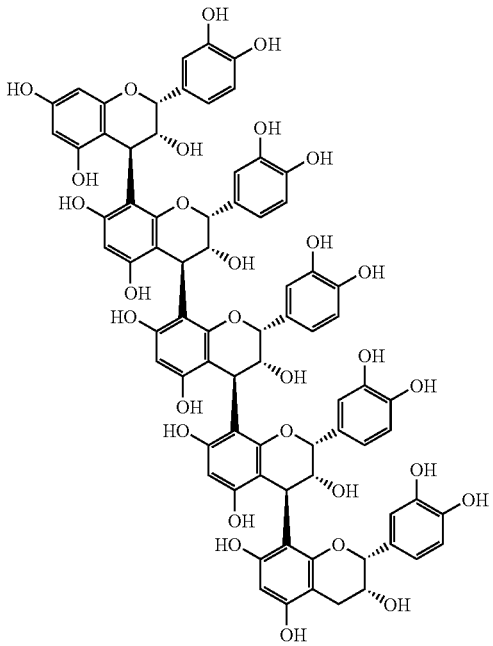

As used herein, a "cell cycle regulatory protein" is a protein that either directly or indirectly regulates the cell cycle. Examples of proteins that regulate the cell cycle directly are Cdc2, p53 and retinoblastoma protein (pRb), and an example of a protein that regulates the cell cycle indirectly is forkhead transcription factor (FKHR). Thus, in certain embodiments, a method of inducing, promoting or stimulating dephosphorylation of a hyperphosphorylated cell cycle regulatory protein in a tumor cell would involve Cdc2, p53, pRb and/or FKHR. More specifically, the methods involve inducing, promoting or stimulating dephosphorylation of hyperphosphorylated Cdc2 at amino acid position Tyr15, hyperphosphorylated p53 at amino acid position Ser392, hyperphosphorylated FKHR at amino acid position Ser 256, and hyperphosphorylated pRb at at least one of amino acid positions Ser 780, Ser795, and Ser 807/811.

The phrase "hyperphosphorylated cell cycle regulatory protein" refers to a cell cycle regulatory protein whose phosphorylation status is abnormal (i.e., unlike the one found in a normally functioning cell) resulting in an altered function of the protein and changes in the cell cycle. It will be understood that "hyperphosphorylation" contributes to transformation of a normal cell to a tumor cell, i.e., it is a contributing factor leading to tumorigenesis and a tumor phenotype of the cell.

The invention also relates to a method of treating a tumor in which hyperphosphorylation of a cell cycle regulatory protein contributed to the tumor phenotype, comprising administering to a human or a veterinary animal suffering from said tumor an effective amount of a compound having the formula $A_n$, or a pharmaceutically acceptable salt or derivative thereof (including oxidation products):

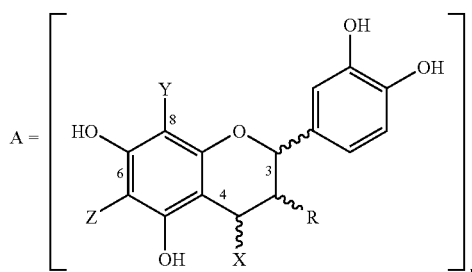

wherein n is an integer from 2 to 18;

R and X each have either α or β stereochemistry;

R is OH, O-sugar or O-gallate;

the substituents of C-4, C-6 and C-8 are X, Z and Y, respectively, and bonding of monomeric units occurs at C-4, C-6 or C-8;

when any C-4, C-6 or C-8 is not bonded to another monomeric unit, X, Y and Z are hydrogen or a sugar; and the sugar is optionally substituted with a phenolic moiety at any position, for instance, via an ester bond.

For example, the above method may involve administration of a compound $A_n$, or a pharmaceutically acceptable salt or derivative thereof (including oxidation products), wherein R is OH, and when any C-4, C-6 or C-8 is not bonded to another monomeric unit, X, Y and Z are hydrogen. In some embodiments of the above method, the sugar in the formula $A_n$ is preferably a monosaccharide or di-saccharide. Examples of suitable sugars are glucose, galactose, rhamnose, xylose, and arabinose. Examples of phenolic moieties are as described above.

In one embodiment, a method of treating a tumor in which hyperphosphorylation of a cell cycle regulatory protein contributed to the tumor phenotype, comprises administering to a human or a veterinary animal suffering from said tumor an effective amount of a compound having the formula $A_n$, or a pharmaceutically acceptable salt or derivative thereof (including oxidation products):

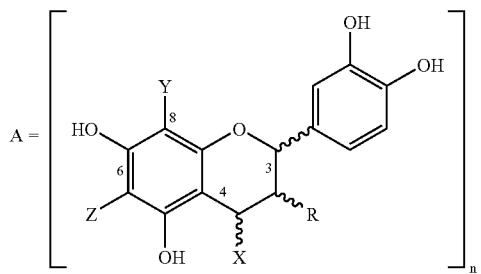

wherein n is 5;

R and X each have either α or β stereochemistry;

R is OH;

the substituents of C-4, C-6 and C-8 are X, Z and Y, respectively, and bonding of monomeric units occurs at C-4, C-6 and C-8; and when any C-4, C-6 or C-8 are not bonded to another monomeric unit, X, Y and Z are hydrogen.

Examples of the pentamers may be: [EC-(4β→8)]$_4$-EC, [EC-(4β→8)]$_3$-EC-(4β→6)-EC, [EC-(4β→8)]$_3$-EC-(4β→8)-C, and [EC-(4β→8)]$_3$-EC-(4β→6)-C, wherein EC is epicatechin and C is catechin.

In one example, pentamer has the following formula:

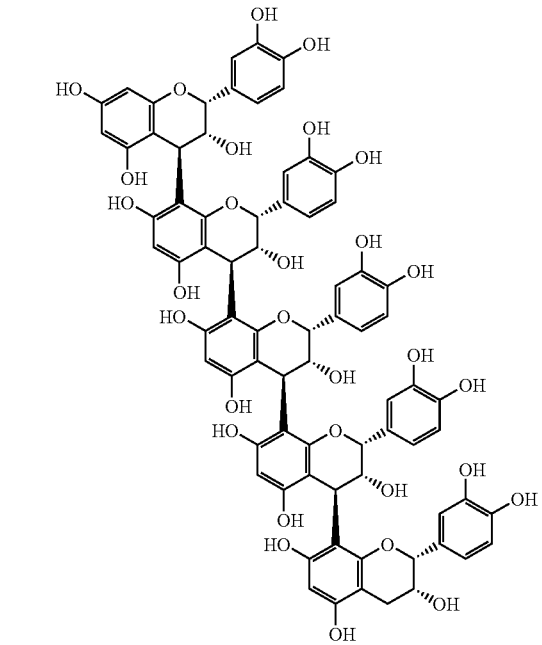

As used herein, "treatment" means improving an existing medical condition, for example, a tumor in which hyperphosphorylation of a cell cycle regulatory protein contributed to the tumor phenotype, for example by slowing down the disease progression, prolonging survival, reducing the risk of death, and/or inducing a measurable reduction in a phosphorylation status of the relevant cell cycle regulatory protein.

The above treatment methods involve, for example, treating a tumor in which hyperphosphorylation of Cdc2, p53, pRb and/or FKHR contributed to the tumor phenotype. More specifically, the methods may involve treatment of tumors wherein hyperphosphorylated Cdc2 at amino acid position Tyr15, hyperphosphorylated p53 at amino acid position Ser392, hyperphosphorylated FKHR at amino acid position Ser 256, and/or hyperphosphorylated pRb at at least one of amino acid positions Ser 780, Ser795, and Ser 807/811 contributed to the tumor phenotype. Examples of tumors to be treated are breast, ovarian and colon cancer.

The phrase "a tumor in which hyperphosphorylation of a cell cycle regulatory protein contributed to the tumor phenotype" refers to a tumor that developed when hyperphosphorylated cell cycle regulatory protein was at least one of the factors leading to tumorigenesis.

The present invention also covers a method of treating tumor, particularly cancer, in a human suffering from a tumor which overexpresses p53, which is hyperphosphorylated at at least amino acid position Ser392. Examples of such cancers are breast and colon cancers.

A method of treating a cancer which overexpresses AKT kinase in a human or a veterinary animal is also provided. Examples of such cancers are ovarian, breast, prostate, lung, pancreatic, liver and colorectal cancers overexpressing AKT. Patients that overexpress AKT kinase are suitable for treatment with the present compounds because AKT, which is one of cancer prognostic markers, phosphorylates FKHR at amino acid position Ser256 and inhibits it, thus preventing the cell from proceeding toward apoptosis. The present compounds are also suitable for combination therapy with AKT inhibitors. Examples of AKT inhibitors include SRI International's experimental drug SR13668.

A method of treating tumor, particularly cancer, which overexpresses cyclin D1, in a human or a veterinary animal is also provided. An example of such cancer is breast cancer overexpressing cyclin D1; such overexpression occurs in about 50% of breast cancer patients. Cyclin D1 plays a critical role in tumorigenesis and differentiation. The cyclin D1 gene encodes a regulatory subunit of a holoenzyme that phosphorylates and inactivates the tumor suppressor protein pRb. Thus, patients that overexpress cyclin D1 are suitable for treatment with the present compounds. The present compounds are also suitable for combination therapy with chemotherapeutic agents that target cyclin D1. Examples of such agents are retinoids, natural and synthetic derivatives of vitamin A, repress cyclin D1. See Petty et al., *Lung Cancer*, 2003 August; 41 Suppl 1: S155-61, the pre-clinical and clinical studies described therein are incorporated herein by reference.

Also within the scope of the invention is a method of treating tumor, particularly cancer, in a human or a veterinary animal suffering from cancer which is resistant to treatment with paclitaxel (Taxol®). Phosphorylation of Tyr15 of Cdc2 by ErbB2 inhibits Cdc2 activation and is involved in resistance to paclitaxel-induced apoptosis. Since the compounds of the invention can dephosphorylate Cdc2 at Tyr15, patients resistant to paclitaxel can be treated. The present compounds may be administered alone or in a combination therapy with paclitaxel.

Any of the above methods may be practiced using the compounds of the invention and at least one additional chemotherapeutic agent. In addition to the chemotherapeutic agents mentioned above, e.g. AKT and cyclin D1 inhibitors, growth factor inhibitors may also be used. Inhibitors of epidermal growth factor receptor (EGFR), insulin growth factor receptor (IGFR) and Her-2 are exemplary. Examples of such agents are inhibitors of tyrosine kinase receptors, e.g. C225, an anti-EGFR monoclonal antibody (Overholser et al., *Cancer* Jul. 1, 2000;89(1):74-82) and trastuzumab (Herceptin®, Genentech), a monoclonal antibody against ErbB2 receptor that is effective and is prescribed to breast cancer patients that over-express the receptor; competitive inhibitors of adenosine triphosphate binding sites on tyrosine and serine/threonine kinases, e.g. ZD1839 (also known as gefitinib or Iressa®, see www.clinicaltrials.gov); OSI-774 (Tarceva™; see Prados et al., 9th ASCO Annual Meeting, Chicago, Ill., May 31-Jun. 3, 2003 (Clinical Study, Abstract No. 394); CI-1033, an ErbB2 inhibitor (see clinicaltrials.gov), the above references hereby incorporated herein by reference.

The present compounds may be administered, in some embodiments, to enhance responsiveness to chemotherapeutic agents and/or methods. For that purpose, dosage forms other than pharmaceuticals, e.g. dietary supplements and foods, may also be used.

The invention also encompasses a method of preventing tumor, particularly cancer, (chemoprevention) by inducing dephosphorylation of a hyperphosphorylated cell cycle regulatory protein in a subject at risk of developing tumor (in which hyperphosphorylation of a cell cycle regulatory protein contributed to the tumor phenotype) by administering the compounds of the invention.

The term "preventing" means reducing the risks associated with developing a disease, including reducing the onset of the disease.

The phrase "subject at risk of developing tumor" means a subject with a characteristic(s) which increases the likelihood of tumor in a group of people who have a risk factor for developing the tumor compared to an otherwise healthy group of people who do not. Risk factors may be exposure to UV radiation or chemical agents.

The above described methods may be used in a human or a veterinary animal, such as a dog, a cat, and a horse.

Thus, the following uses are within the scope of the invention. Use of the compound $A_n$, or a pharmaceutically acceptable salt or derivative thereof (including oxidation products), as defined above, in the manufacture of a medicament, food, nutraceutical or dietary supplement for use for inducing dephosphorylation of a hyperphosphorylated cell cycle regulatory protein in a tumor cell in which hyperphosphorylation of said protein contributed to transformation. Use of the compound $A_n$, or a pharmaceutically acceptable salt or derivative thereof (including oxidation products), as defined above, in the manufacture of a medicament, food, nutraceutical or dietary supplement for use in treating tumor in which hyperphosphorylation of a cell cycle regulatory protein contributed to the tumor phenotype. Examples of cell cycle regulatory proteins are Cdc2, p53, FKHR and pRb.

The following uses are representative of some embodiments. Use of a compound of formula $A_n$, or a pharmaceutically acceptable salt or derivative thereof (including oxidation products), as defined herein, in the manufacture of a medicament, food, nutraceutical or dietary supplement for use in treating tumors which overexpresses p53 which is hyperphosphorylated at at least amino acid position Ser392. Use of a compound of formula $A_n$, or a pharmaceutically acceptable salt or derivative thereof (including oxidation products), as defined herein, in the manufacture of a medicament, food, nutraceutical or dietary supplement for use in treating tumor which overexpresses cyclin D1. Use of a compound of formula $A_n$, or a pharmaceutically acceptable salt or derivative thereof (including oxidation products), as defined herein, in the manufacture of a medicament, food, nutraceutical or dietary supplement for use in treating tumor which overexpresses AKT. Use of a compound of formula $A_n$, or a pharmaceutically acceptable salt or derivative thereof (including oxidation products), as defined herein, in the manufacture of a medicament, food, nutraceutical or dietary supplement for use in treating cancer which is resistant to treatment with paclitaxel (Taxol®).

The above described methods may further comprise determining the effectiveness of the treatment by, for example, assaying the phosphorylation status of the cell cycle regulatory protein whose hyperphosphorylation is being treated.

The advantage of the present invention is that it offers a personalized medicine approach to the treatment of tumors particularly cancers. Each patient can be evaluated for his/her expression and phosphorylation status of the cell cycle regulatory proteins and where appropriate the compounds and methods of the present invention may be applied. Thus, methods of profiling of the patients and their subsequent treatment are also within the scope of the invention.

It will be understood by a person of skill in the art that overexpression in subjects to be profiled and/or treated can be determined using methods and reagents well known in the art. For example, overexpression can be detected using Western blotting with appropriate antibodies (e.g. anti-AKT or anti-cyclin D1 antibodies) or, if the overexpression is at the level of transcription, using Southern and Northern blotting with appropriate nucleic acid probes. Hyperphosphorylation may be detected using antibodies that recognize phosphorylated amino acid residues. Examples of these methods are also shown in Example 3.

The effective amount may be determined by a person of skill in the art using the guidance provided herein and general knowledge in the art. For example, the effective amount may be such as to achieve a physiologically relevant concentration in the body of a mammal. Such a physiologically relevant concentration may be at least 20 nanomolar (nM), preferably at least about 100 nM, and more preferably at least about 500 nM. In one embodiment, at least about one micromole in the blood of the mammal, such as a human, is achieved. The compounds of formula $A_n$, as defined herein, may be administered at from about 50 mg/day to about 1000 mg/day, preferably from about 100-150 mg/day to about 900 mg/day, and most preferably from about 300 mg/day to about 500 mg/day. However, amounts higher than stated above may be used.

The treatments/preventive administration may be continued as a regimen, i.e., for an effective period of time, e.g., daily, monthly, bimonthly, biannually, annually, or in some other regimen, as determined by the skilled medical practitioner for such time as is necessary. The administration may be continued for at least a period of time required to reduce hyperphosphorylation to a therapeutically relevant levels. Preferably, the composition is administered daily, most preferably two or three times a day, for example, morning and evening to maintain the levels of the effective compounds in the body of the mammal. To obtain the most beneficial results, the composition may be administered for at least about 30, or at least about 60 days. These regiments may be repeated periodically.

Compositions and Formulations

The inventive compounds may be from different sources, of natural origin (e.g. genus *Theobroma*, genus *Herrania*) or synthetically prepared. In certain embodiments the compounds are derived from cocoa, including cocoa flavanols and/or cocoa procyanidin oligomers. In addition to, or in place of, the cocoa polyphenols, compositions may contain polyphenols from sources other than cocoa, which have structures and/or properties same or similar to those of cocoa polyphenols.

As used herein, the term "cocoa polyphenol" (CP) refers to polyphenolic substances such as flavanols and their related oligomers which are characteristic of cocoa beans. In other words, a cocoa polyphenol, a cocoa flavanol or a cocoa procyanidin oligomer is any such polyphenol, flavanol or procyanidin oligomer, irrespective of its source, which has a structural formula of the polyphenol, flavanol or procyanidin naturally occurring in cocoa. In one embodiment, these compounds may be extracted from cocoa beans or cocoa ingredients. The term "flavanol" includes the monomers catechin and epicatechin. Oligomers of catechin and epicatechin are referred to as procyanidins. Any reference to polyphenol herein should be understood to also apply to flavanols and procyanidin, in combination and individually, and vice versa.

The term "cocoa ingredient" refers to a cocoa solids-containing material derived from shell-free cocoa nibs such as chocolate liquor and partially or fully-defatted cocoa solids (e.g. cake or powder).

The polyphenols for use in the present invention may be of natural origin, for example, derived from a cocoa bean or another natural source of polyphenols, or prepared synthetically. A person of skill in the art may select natural or synthetic polyphenol based on availability or cost. Polyphenols may be included in the composition in the form of a cocoa ingredient containing cocoa polyphenols, for example, chocolate liquor included in chocolate, or may be added independently of cocoa ingredients, for example, as an extract, extract fraction, isolated and purified individual compound, pooled extract fractions or a synthetically prepared compound.

The procyanidin oligomers may have from 2 to about 18, preferably from 2 to about 12, and most preferably from 2 to about 10 monomeric units. Alternatively, the oligomers may have from 3-18, preferably 3-12, and more preferably 3-10 monomeric units; or from 5-18, preferably 5-12 and more preferably 5-10 monomeric units. For example, oligomers may be dimers, trimers, tetramers, pentamers, hexamers, heptamers, octamers, nonamers and decamers. In the oligomer, monomers are connected via interflavan linkages of (4→6) and/or (4→8). Oligomers with exclusively (4→8) linkages are linear; while the presence of at least one (4→6) bond results in a branched oligomer. Also within the scope of the invention are oligomers comprising at least one non-natural linkage (6→6), (6→8), and (8→8). The synthesis of such non-naturally occurring oligomers is described in the International Appl. No. PCT/US00/08234 published on Oct. 19, 2000 as WO 00/61547, the relevant portions of which are hereby incorporated herein by reference. Flavan-3-ol (monomeric) units in any of the compounds of the invention may be (+)-catechin, (−)-epicatechin and their respective epimers (e.g. (−)-catechin and (+)-epicatechin)).

The cocoa polyphenol may be prepared by extraction from cocoa beans, cocoa nibs, or cocoa ingredients such as chocolate liquor, partially defatted cocoa solids, and/or fully defatted cocoa solids. Preferably, the extract is prepared from a fully or partially defatted cocoa powder. Beans from any species of *Theobroma, Herrania* or inter- and intra-species crosses thereof may be used. The extract may be prepared from fermented, underfermented or unfermented beans, the fermented beans having the least amount of cocoa polyphenols and the unfermented the most. The selection of beans may be made based on the fermentation factor of the beans, for example, the extract may be made from the beans having a fermentation factor of about 275 or less. Optimizing the level of polyphenols in the cocoa ingredient and extract thereof by manipulating the degree of fermentation may be done as described in the International Appl. No. PCT/US97/15893 published as WO98/09533, the relevant portions of which are hereby incorporated herein by reference.

Cocoa polyphenols may be extracted from cocoa ingredients that have been processed using traditional methods of cocoa processing (described, for example, in Industrial Chocolate Manufacture and Use, ed. Beckett, S. T., Blackie Acad. & Professional, New York, 1997, such as in Chapters 1, 5 and 6) or using an improved processing method described in U.S. Pat. No. 6,015,913 to Kealey et al. that preserves polyphenols (by preventing their destruction) in cocoa ingredients in contrast to the traditional methods. The improved cocoa processing method omits the traditional roasting step. Thus, cocoa ingredients obtainable by (a) heating the cocoa bean for a time and a temperature sufficient to loosen the cocoa shell without roasting the cocoa nib; (b) winnowing the cocoa nib from the cocoa shell; (c) screw pressing the cocoa nib and (d) recovering the cocoa butter and partially defatted cocoa solids which contain preserved levels of cocoa polyphenols, may be used. The method retains a much higher level of higher procyanidin oligomers than traditional processing methods. Cocoa solids produced by this method may contain greater than 20,000 µg of total flavanol and/or procyanidins per gram nonfat solids; preferably greater than 25,000 µg/g, more preferably greater than 28,000 µg/g, and most preferably greater than 30,000 µg/g. For purposes of this invention, the total flavanol and/or procyanidin amounts are determined as described in Example 2.

Polyphenols may be extracted from the sources indicated above, or any other polyphenol or flavanol or procyanidin containing source, using solvents in which the polyphenols dissolve. Suitable solvents include water or organic solvent such as methanol, ethanol, acetone, isopropyl alcohol and ethyl acetate. Solvent mixtures may also be used. When water is used as the solvent, it may be slightly acidified, for example with acetic acid. Examples of some solvents are mixtures of water and organic solvent, for example aqueous methanol, ethanol or acetone. Aqueous organic solvents may contain, for example, from about 50% to about 95% of organic solvent. Thus, about 50%, about 60%, about 70%, about 80% and about 90% organic solvent in water may be used. The solvent may also contain a small amount of acid such as acetic acid, for example, in the amount of about 0.5% to about 1.0%. The composition of the extracts, i.e., the representation (i.e., oligomeric profile) and the amount of procyanidin oligomers, will depend on the choice of solvents. For example, the water extract contains primarily monomers, the ethyl acetate extract contains monomers and lower oligomers, mainly dimers and trimers, and the aqueous methanol, ethanol or acetone extract contains monomers and a range of higher oligomers. One of the solvents for extraction of monomer as well as higher procyanidin oligomers is about 70% acetone. However, any extract containing polyphenols is useful in the invention. The methods of cocoa polyphenol extraction are known in the art and are described, for example, in the U.S. Pat. No. 5,554,645 to Romanczyk et al. and the International Appl. No. PCT/US97/05693, published as WO97/36497. Thus, in one embodiment, the cocoa extract is prepared by reducing cocoa beans to cocoa powder, defatting the powder, extracting the cocoa polyphenols, and purifying the extract. The cocoa powder can be prepared by freeze-drying the cocoa beans and pulp, depulping and dehulling the freeze-dried cocoa beans, and grinding the dehulled beans.

The cocoa polyphenol extract may be purified, for example, by removal of the caffeine and/or theobromine, and further purified by gel permeation chromatography and/or High Pressure Liquid Chromatography (HPLC). Gel permeation chromatography (e.g. on Sephadex LH-20) may be used to enrich the extract for higher procyanidin oligomers. For example, the eluate containing monomers and lower oligomers may not be collected until the oligomer(s) of choice begins eluting from the column. An example of such an extract is known in the art and is described in Example 5 of the International Appl. No. PCT/US97/05693, published as WO97/36497, the relevant portions of which are hereby incorporated by reference herein. By using preparative HPLC, for example, normal phase HPLC, the extract may be fractionated, for example, into monomeric and oligomeric fractions containing at least 50% by weight of the monomer or specific oligomer(s). When a particular fraction contains the monomers or any of the lower oligomers (e.g. dimers, trimers or tetramers fraction), the fraction contain about 90 to 95% by weight of the particular oligomeric fraction. The desired fractions may be pooled after separation to obtain a combination of oligomers of choice for example to contain oligomers 3-10 or 5-10. A person of skill in the art can manipulate the chromatographic conditions to achieve the desired procyanidin profile in view of the guidance in this specification, general knowledge in the art and, for example, the teachings of U.S. Pat. No. 5,554,645 to Romanczyk et al. and the International Appl. No. PCT/US97/05693, published as WO97/36497.

The monomeric fraction typically contains a mixture of monomers epicatechin and catechin; and the oligomeric fraction typically contains a mixture of dimers (in a dimer fraction), trimers (in a trimer fraction), tetramers (in a tetramer fraction), etc. Mixtures of monomers and oligomers occur in isolated fractions because cocoa contains more than one type of each of monomer, dimer, etc. The oligomeric variability occurs as a result of two monomers, epicatechin and catechin, that are building blocks of procyanidins, as well as the chemical bond connecting monomers in the oligomer. Thus, cocoa dimers are primarily B2 and B5, each of which contains two monomers of epicatechin. Individual monomers and oligomers may be obtained using reversed-phase HPLC, e.g. using a C18 column.

Cocoa polyphenol may be used in the compositions of the invention as a cocoa extract, e.g. solvent-derived extract, cocoa fraction, isolated compounds or in the form of a cocoa ingredient or a chocolate containing an effective amount of cocoa flavanols and/or procyanidins. The cocoa ingredients may be prepared using traditional cocoa processing procedures but is preferably prepared using the method described in U.S. Pat. No. 6,015,913 to Kealey et al. Alternatively, to enhance the level of cocoa polyphenols, chocolate liquor and cocoa solids prepared from cocoa beans having a fermentation factor of about 275 or less may be used. These ingredients have cocoa polyphenol content that is higher than can be obtained using traditional cocoa processing methods (e.g. with roasting) and fully fermented beans. The chocolate may be prepared using conventional techniques from the ingredients described above or using an improved process for preserving cocoa polyphenols during chocolate manufacturing as described in the International Appl. No. PCT/US99/05414 published as WO99/45788, the relevant portions of which are hereby incorporated herein by reference. A chocolate prepared by at least one of the following non-traditional processes is referred to herein as a "chocolate having a conserved amount of cocoa polyphenols": (i) preparing cocoa ingredients from underfermented or unfermented cocoa beans; (ii) preserving cocoa polyphenol during cocoa ingredient manufacturing process; and (iii) preserving cocoa polyphenol during chocolate manufacturing process.

Synthetic procyanidins may also be used and are prepared by methods known in the art and as described for example in the International Appl. No. PCT/US98/21392 published as WO99/19319, the relevant portions of which are hereby incorporated herein by reference. Flavanol and/or procyanidin derivatives may also be useful. These include esters of monomer and oligomers such as the gallate esters (e.g. epicatechin gallate and catechin gallate); compounds derivatized with a saccharide moiety such as mono- or di-saccharide moiety (e.g. β-D-glucose), for example at positions X, Y and/or Z in the above formulas; glycosylated monomers and oligomers, and mixtures thereof; metabolites of the procyanidin monomers and oligomers, such as the sulphated, glucouronidated, and methylated forms except for the enzyme cleavage products of procyanidins generated by colonic microflora metabolism. The derivatives may be from natural sources or prepared synthetically.

The composition of the invention is useful as a pharmaceutical, a food, a food additive, or a dietary supplement.

The compositions may contain a carrier, a diluent, or an excipient. Depending on the intended use, the carrier, diluent, or excipient may be chosen to be suitable for human or veterinary use, food, additive, supplement or pharmaceutical use. The composition may optionally contain an additional cancer treating agent.

As used herein a "food" is a material consisting essentially of protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993. The term food includes a beverage adapted for human or animal consumption. As used herein a "food additive" is as defined by the FDA in 21 C.F.R. 170.3(e)(1) and includes direct and indirect additives. As used herein, a "pharmaceutical" is a medicinal drug. See Merriam-Webster's Collegiate Dictionary, 10th Edition, 1993. A pharmaceutical may also be referred to as a medicament. As used herein, a "dietary supplement" is a product (other than tobacco) that is intended to supplement the diet that bears or contains the one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients.

Any conventional food including any beverage which has been improved by the presence of a polyphenol or a derivative thereof, e.g. methylated compounds or metabolic breakdown products, and optionally in combination with another cancer treating/chemopreventive agent. Other compounds, such as L-arginine, calcium, potassium, magnesium, and anti-oxidants such as vitamin E and vitamin C, any of the vitamins of the B complex, a carotenoid, guar gum, and/or a mono or polyunsaturated fatty acid (e.g. omega-3), may also be present.

The improvement is achieved either (i) by adding polyphenol or a derivative thereof to a food that does not contain cocoa polyphenol or (ii) when the food traditionally may contain cocoa polyphenols, such as for example chocolate, by enhancing the polyphenol level over the one found in the traditionally prepared food. The enhancement may be achieved by adding additional polyphenols such as cocoa polyphenols, for example, in a form of an extract, fraction or isolated and purified compound there from; by adding cocoa polyphenol in combination with another polyphenol containing ingredient (e.g. nut skins); by manipulating the cocoa ingredients processing and cocoa bean selection, as described above, to preserve cocoa polyphenol in the cocoa ingredient used for the manufacture of the food product; or by manipulating the chocolate manufacturing process as described above. Thus, these foods (including beverages) contain an "elevated level of polyphenols" (including cocoa procyanidins) in comparison to comparative conventional foods (including beverages). An example of a chocolate having an elevated level of polyphenol occurs when a chocolate manufacturer adds a cocoa extract containing cocoa polyphenols to its previously commercially available product. The foods may also be referred to as "high cocoa polyphenol foods," i.e., they contain higher levels of polyphenol than their traditional counterparts.

The foods comprising cocoa polyphenols, or any of the compounds described herein, and optionally another tumor/cancer treating agent may be adapted for human or veterinary use, and include pet foods. The food may be other than a confectionery, however, the preferred cholesterol lowering food is a confectionery such as a standard of identity (SOI) and non-SOI chocolate, such as milk, sweet and semi-sweet chocolate including dark chocolate, low fat chocolate and a candy which may be a chocolate covered candy. Other examples include a baked product (e.g. brownie, baked snack, cookie, biscuit) a condiment, a granola bar, a toffee chew, a meal replacement bar, a spread, a syrup, a powder beverage mix, a cocoa or a chocolate flavored beverage, a pudding, a rice cake, a rice mix, a savory sauce and the like. If desired, the foods may be chocolate or cocoa flavored. Food products may be chocolates and candy bars, such as granola bars, containing nuts, for example, peanuts, walnuts, almonds, and hazelnuts. It should be noted that the addition of nuts with skins to the food described herein may also increase the total polyphenol content since, for example, peanut skins contain about 17% flavanols and procyanidins and almond skins contain about 30% flavanols and procyanidins. In one embodiment, the nut skins are added to the nougat of a chocolate candy.

In certain embodiments, the non-chocolate food product contains from about at least 5 micrograms/g to about 10 mg/g, and, for example, at least 5 micrograms/g food product, preferably at least 10 microgram/g, more preferably at least 100 micrograms/g of cocoa flavanols and/or procyanidin oligomers. If desired, the non-chocolate food products can contain much higher levels of cocoa procyanidins than those found in the chocolate food products described below.

The chocolate confectionery may be milk or dark chocolate. In certain embodiments, the chocolate comprises at least 3,600 micrograms, preferably at least 4,000 micrograms, preferably at least 4,500 micrograms, more preferably at least 5,000 micrograms, and most preferably at least 5,500 micrograms inventive compounds (e.g. cocoa procyanidins) each per gram of chocolate, based on the total amount of nonfat cocoa solids in the product. In other embodiments, the chocolate contains at least 6,000 micrograms, preferably at least 6,500 micrograms, more preferably at least 7,000 micrograms, and most preferably at least 8,000 micrograms of cocoa procyanidins per gram, and even more preferably 10,000 micrograms/g based on the nonfat cocoa solids in the product.

A milk chocolate confectionery may have at least 1,000 micrograms, preferably at least 1,250 micrograms, more preferably at least 1,500 micrograms, and most preferably at least 2,000 micrograms cocoa flavanols and/or procyanidins each per gram of milk chocolate, based on the total amount of nonfat cocoa solids in the milk chocolate product. In the preferred embodiment, the milk chocolate contains at least 2,500 micrograms, preferably at least 3,000 micrograms, more preferably at least 4,000 micrograms, and most preferably at least 5,000 micrograms cocoa flavanols and/or procyanidins each per gram of milk chocolate, based on the total amount of nonfat cocoa solids in the milk chocolate product.

The amount of L-arginine in the food products can vary. Typically, cocoa contains between 1 to 1.1 grams of L-arginine per 100 grams of partially defatted cocoa solids. It can range from 0.8 to 1.5 per 100 grams of cocoa. In some embodiments, the chocolate food products of this invention contain L-arginine in an amount greater than that which naturally occurs in the cocoa ingredients. Knowing the amount of cocoa ingredients and L-arginine used in the food product, one of ordinary skill in the art can readily determine the total amount of L-arginine in the final product. The food product will generally contain at least 5 micrograms /g, preferably at least 30 micrograms /g, or at least 60 micrograms/g, even more preferably at least 200 micrograms /g food product.

A daily effective amount of a polyphenol of the invention such as flavanols and/or procyanidins may be provided in a single serving. Thus, a confectionery (e.g. chocolate) may contain at least about 100 mg/serving (e.g. 150-200, 200-400 mg/serving) cocoa procyanidins.

Pharmaceuticals containing the inventive compounds, optionally in combination with another cancer treating agent, may be administered in a variety of ways such as orally, sublingually, bucally, nasally, rectally, intravenously, parenterally and topically. A person of skill in the art will be able to determine a suitable mode of administration to maximize the delivery of the compound of formula $A_n$, and optionally another cancer treating agent, to the site of the tumor. Thus, dosage forms adapted for each type of administration are within the scope of the invention and include solid, liquid and semi-solid dosage forms, such as tablets, capsules, gelatin capsules (gelcaps), bulk or unit dose powders or granules, emulsions, suspensions, pastes, creams, gels, foams or jellies. Sustained-release dosage forms are also within the scope of the invention and may be prepared as described in U.S. Pat. Nos. 5,024,843; 5,091,190; 5,082,668; 4,612,008 and 4,327,725, relevant portions of which are hereby incorporated herein by reference. Suitable pharmaceutically acceptable carriers, diluents, or excipients are generally known in the art and can be determined readily by a person skilled in the art. The tablet, for example, may comprise an effective amount of the polyphenol-containing composition and optionally a carrier, such as sorbitol, lactose, cellulose, or dicalcium phosphate.

The dietary supplement containing cocoa flavanol and/or procyanidin, and optionally another cancer treating agent, may be prepared using methods known in the art and may comprise, for example, nutrient such as dicalcium phosphate, magnesium stearate, calcium nitrate, vitamins, and minerals.

Further within the scope of the invention is an article of manufacture such as a packaged product comprising the composition of the invention (e.g. a food, a dietary supplement, a pharmaceutical) and a label indicating the presence of, or an enhanced content of the inventive compounds or directing use of the composition to treat tumor (e.g. cancer) in which hyperphosphorylation of a cell cycle regulatory protein contributed to the tumor phenotype. The packaged product may contain the composition and the instructions for use to treat tumor (e.g. cancer) in which hyperphosphorylation of a cell cycle regulatory protein contributed to the tumor phenotype. The label and/or instructions for use may refer to any of the methods of use described in this application, In certain embodiments, the label and/or the instructions for use direct use of the compounds of the invention for treating tumors which overexpresses p53 (which is hyperphosphorylated at at least amino acid position Ser392); tumor which overexpresses cyclin D1; tumor which overexpresses Akt; or tumors which are resistant to treatment with paclitaxel (Taxol®).

Also within the scope of the invention is an article of manufacture (such as a packaged product or kit) adapted for use in combination therapy comprising at least one container and at least one compound of the invention (e.g. compound of formula $A_n$ wherein n is 5; procyanidin pentamer). The article of manufacture further comprises at least one additional chemotherapeutic agent (i.e., other than the compound of formula $A_n$, or a pharmaceutically acceptable salt or derivative thereof (including oxidation products)), which chemotherapeutic agent may be provided as a separate composition, in a separate container, or in admixture with the compound of the invention.

The invention is further described in the following non-limiting examples.

EXAMPLES

Example 1

Extraction and Purification

The extraction and purification may be conducted as described in U.S. Pat. No. 6,670,390 to Romanczyk et al., which is hereby incorporated herein by reference. Certain relevant portions are reproduced below.

Procyanidin Extraction Procedures

Method 1

Procyanidins were extracted from the defatted, unfermented, freeze dried cocoa beans using a modification of the method described by Jalal and Collin ('Polyphenols of Mature Plant, Seedling and Tissue Cultures of Theobroma Cacoa, Phytochemistry, 6, 1377-1380, 1977). Procyanidins were extracted from 50 gram batches of the defatted cocoa mass with 2×400 mL 70% acetone/deionized water followed by 400 mL 70% methanol/deionized water. The extracts were pooled and the solvents removed by evaporation at 45° C. with a rotary evaporator held under partial vacuum. The resultant aqueous phase was diluted to 1 L with deionized water and extracted 2× with 400 mL $CHCl_3$. The solvent phase was discarded. The aqueous phase was then extracted 4× with 500 mL ethyl acetate. Any resultant emulsions were broken by centrifugation on a Sorvall RC 28S centrifuge operated at 2,000× for 30 min. at 10° C. To the combined ethyl acetate extracts, 100-200 mL deionized water was added. The solvent was removed by evaporation at 45° C. with a rotary evaporator held under partial vacuum. The resultant aqueous phase was frozen in liquid $N_2$ followed by freeze drying on a LABCONCO Freeze Dry System. The yields of crude procyanidins that were obtained from the different cocoa genotypes are listed in Table 1.

TABLE 1

Crude Procyanidin Yields

| GENOTYPE | ORIGIN | HORTICULTUREAL RACE |
|---|---|---|
| UIT-1 | Malaysia | 3.81 |
| Unknown | West Africa | 2.55 |
| ICS-100 | Brazil | 3.42 |
| ICS-39 | Brazil | 3.45 |
| UF-613 | Brazil | 2.98 |
| EEG-48 | Brazil | 3.15 |
| UF-12 | Brazil | 1.21 |
| NA-33 | Brazil | 2.23 |

Method 2

Alternatively, procyanidins are extracted from defatted, unfermented, freeze dried cocoa beans with 70% aqueous acetone. Ten grams of defatted material was slurried with 100 mL solvent for 5-10 min. The slurry was centrifuged for 15 min. at 4° C. at 3000×g and the supernatant passed through glass wool. The filtrate was subjected to distillation under partial vacuum and the resultant aqueous phase frozen in liquid $N_2$, followed by freeze drying on a LABCONCO Freeze Dry System. The yields of crude procyanidins ranged from 15-20%.

Without wishing to be bound by any particular theory, it is believed that the differences in crude yields reflected variations encountered with different genotypes, geographical origin, horticultural race, and method of preparation.

Partial Purification of Cocoa Procyanidins

A. Gel Permeation Chromatography

Procyanidins obtained as described above were partially purified by liquid chromatography on Sephadex LH-20 (28.times.2.5 cm). Separations were aided by a step gradient from deionized water into methanol. The initial gradient composition started with 15% methanol in deionized water which was followed step wise every 30 min. with 25% methanol in deionized water, 35% methanol in deionized water, 70% methanol in deionized water, and finally 100% methanol. The effluent following the elution of the xanthine alkaloids (caffeine and theobromine) was collected as a single fraction. The fraction yielded a xanthine alkaloid free subfraction which was submitted to further subfractionation to yield five subfractions designated MM2A through MM2E. The solvent was removed from each subfraction by evaporation at 45° C. with a rotary evaporator held under partial vacuum. The resultant aqueous phase was frozen in liquid $N_2$ and freeze dried overnight on a LABCONCO Freeze Dry System Approximately, 100 mg of material was subfractionated in this manner. Chromatographic Conditions: Column; 28×2.5 cm Sephadex LH-20, Mobile Phase: Methanol/Water Step Gradient, 15:85, 25:75, 35:65, 70:30, 100:0 Stepped at ½ Hour Intervals, Flow Rate; 1.5 mL/min, Detector; UV at λ1=254 nm and λ2=365 nm, Chart Speed: 0.5 mm/min, Column Load; 120 mg.

B. Semi-preparative High Performance Liquid Chromatography (HPLC)

Method 1. Reverse Phase Separation

Procyanidins obtained as described above were partially purified by semi-preparative HPLC. A Hewlett Packard 1050 HPLC System equipped with a variable wavelength detector, Rheodyne 7010 injection valve with 1 mL injection loop was assembled with a Pharmacia FRAC-100 Fraction Collector. Separations were effected on a Phenomenex Ultracarb™ 10µ ODS column (250×22.5 mm) connected with a Phenomenex 10µ ODS Ultracarb™ (60×10 mm) guard column. The mobile phase composition was: A=water; B=methanol used under the following linear gradient conditions: [Time, % A]; (0,85), (60,50), (90,0), and (110,0) at a flow rate of 5 mL/min. Compounds were detected by UV at 254 nm. Individual peaks or select chromatographic regions were collected on timed intervals or manually by fraction collection for further purification and subsequent evaluation. Injection loads ranged from 25-100 mg of material.

Method 2. Normal Phase Separation

Procyanidin extracts obtained as described above were partially purified by semi-preparative HPLC. A Hewlett Packard 1050 HPLC system, Millipore-Waters Model 480 LC detector set at 254 nm was assembled with a Pharmacia Frac-100 Fraction Collector set in peak mode. Separations were effected on a Supelco 5 pm Supelcosil LC-Si column (250×10 mm) connected with a Supelco 5 µm Supelguard LC-Si guard column (20×4.6 mm). Procyanidins were eluted by a linear gradient under the following conditions: (Time, % A, % B); (0,82,14), (30, 67.6, 28.4), (60, 46, 50), (65, 10, 86), (70, 10, 86) followed by a 10 min re-equilibration. Mobile phase composition was A dichloromethane; B=methanol; and C=acetic acid: water (1:1). A flow rate of 3 mL/min was used. Components were detected by UV at 254 nm, and recorded on a Kipp & Zonan BD41 recorder. Injection volumes ranged from 100-250 µL of 10 mg of procyanidin extracts dissolved in 0.25 mL 70% aqueous acetone. Individual peaks or select chromatographic regions were collected on timed intervals or manually by fraction collection for further purification and subsequent evaluation.

HPLC Conditions: 250×10 mm Supelco Supelcosil LC-Si (5 µm) Semipreparative Column; 20×4.6 mm Supelco Supelcosil LC-Si (5 µm) Guard Column; Detector: Waters LC; Spectrophotometer Model 480 @ 254 nm; Flow rate: 3 mL/min; Column Temperature: ambient; Injection: 250 µL of 70% aqueous acetone extract.

| Gradient: | | | |
|---|---|---|---|
| Time (min) | $CH_2Cl_2$ | Methanol | Acetic Acid:$H_2O$ (1:1) |
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

The fractions obtained were as follows:

| FRACTION | TYPE |
|---|---|
| 1 | dimers |
| 2 | trimers |
| 3 | tetramers |
| 4 | pentamers |
| 5 | hexamers |
| 6 | heptamers |
| 7 | octamers |
| 8 | nonamers |
| 9 | decamers |
| 10 | undecamers |
| 11 | dodecamers |
| 12 | higher oligomers |

Example 2

Determination of Flavanols/Procyanidins

Procyanidins were quantified as follows: a composite standard was made using commercially available (−)-epicatechin, and dimers through decamers obtained in a purified state by the methods described in Hammerstone, J. F. et al., *J. Ag. Food Chem.;* 1999; 47 (10) 490-496; Lazarus, S. A. et al., *J. Ag. Food Chem.;* 1999; 47 (9); 3693-3701; and Adamson, G. E. et al., *J. Ag. Food Chem.;* 1999; 47 (10) 4184-4188. Standard Stock solutions using these compounds were analyzed using the normal-phase HPLC method described in the previously cited Adamson reference, with fluorescence detection at excitation and emission wavelengths of 276 nm and 316 nm, respectively. Peaks were grouped and their areas summed to include contributions from all isomers within any one class of oligomers and calibration curves were generated using a quadratic fit. Monomers and smaller oligomers had almost linear plots which is consistent with prior usage of linear regression to generate monomer-based and dimer-based calibration curves.

These calibration curves were then used to calculate procyanidin levels in samples prepared as follows: First, the cocoa or chocolate sample (about 8 grams) was defatted using three hexane extractions (45 mL each). Next, one gram of defatted material was extracted with 5 mL of the acetone/water/acetic acid mixture (70:29.5:0.5 v/v). The quantity of procyanidins in the defatted material was then determined by comparing the HPLC data from the samples with the calibration curves obtained as described above (which used the purified oligomers). The percentage of fat for the samples (using a one gram sample size for chocolate or one-half gram sample size for liquors) was determined using a standardized method by the Association of Official Analytical Chemists (AOAC Official Method 920.177). The quantity of total procyanidin levels in the original sample (with fat) was then calculated. Calibration was performed prior to each sample run to protect against column-to-column variations.

Example 3

Experimental Procedure

Cell Culture

Human breast cancer cell lines MDA MB-231, MDA MB-436, MD MB-468, SKBR-3 and MCF-7 were obtained from the Lombardi Comprehensive Cancer Center (LCC) Tissue Culture Shared Resource. MDA MB-231, MDA MB-436, MD MB-468 and SKBR-3 are p53-mutated estrogen receptor (ER)-negative cells. MDA MB-231 also contains a mutation in the K-ras oncogene. The MCF-7 cell line is ER-positive and non-mutated for p53. The cells were grown in complete media containing DMEM (Gibco-BRL, Gaithersburg, Md.) supplemented with 10% fetal bovine serum (FBS) (Quality Biological, Gaithersburg, Md.). In addition, media for MCF-7 contained non essential amino acids (Gibco-BRL, Gaithersburg, Md.).

Immortalized human mammary epithelial cells (HMECs), MCF-10A, 184A1N4 and 184B5, normal, finite-life-span HMECs (1001-8, CC-2551) at passage 8, originally derived from mammoplasty breast tissues, were purchased from Clonetics-BioWhittaker, Inc. (Waskersville, Md.). Cell lines generated by introduction of c-MYC, ErbB2 and RAS oncogene into MCF-10A cells (MCF-10A-ErbB2/Ras cells and MCF-10A-c-Myc) were also used.

The MCF-10A cell line (spontaneously immortalized, non-tumorigenic human mammary epithelial cell line with non-mutated p53) was maintained in F-12/DMEM medium supplemented with 5% horse serum (Gibco), 20 ng/mL EGF (Upstate Biotechnology Incorporated, Lake Placid, N.Y.), 10 µg/mL insulin (Biofluids, Rockville, Md.), and 500 ng/mL hydrocortisone. The same media were used for MCF-10A-ErbB2/Ras cells (Ciardiello, F. et al., *Mol Carcinog.*, 6: 43-52. 1992) and MCF-10A-c-Myc cells (Sheen, J-H. et al., *Mol. Cell. Biol.*, 22: 1819-1833, 2002).

The 184A1N4 cell line (hereinafter "A1N4") is a non-tumorigenic cell line derived from primary cultures of HMECs and immortalized with benzo(a)pyrene (provided by Dr. M. R. Stampfer, University of California, Berkley, Calif.) (Stampfer, M. R. et al., *Proc. Natl. Acad. Sci. USA*, 82: 2394-2398, 1985). These cells were maintained in IMEM medium with 0.5% FBS, 0.5 µg/mL of hydrocortisone (Biofluids), 5 µg/mL insulin and 10 ng/mL of EGF.

The 184B5 line is an immortalized, non-tumorogenic cell line derived from primary cultures of HMECs immortalized with benzo(a)pyrene (provided by Dr. M. R. Stampfer) and was maintained in Clonetics mammary epithelial cells medium (MEGM).

Normal mortal HMECs were maintained according to the supplier's instructions in mammary epithelial cell growth medium (CC-3152) (Clonetics) supplemented with 52 µg of bovine pituitary extract per ml, 10 ng/mL of human EGF, 5 µg/mL of insulin, and 0.5 µg/mL of hydrocortisone and were grown in 37° C. incubators with low (0.1 to 0.2%) $CO_2$ settings.

Reagents and Antibodies

HPLC-purified oligomeric pentameric procyanidin was prepared as described in Example 1. The pentameric procyanidin was about 92-95% pure. Stock solutions of pentamer were prepared by first dissolving the pentamer in 20 µL DMSO, followed by dilution to 2 mL with complete media. Sterile filtered aliquots were taken to result in a final concentration of 100 µg/mL.

Rabbit polyclonal poly (ADP-ribose) polymerase (PARP) (H-250) was obtained from Santa Cruz Biotechnology Inc., (Santa Cruz, Calif.). α-Tubulin antibody was obtained from Neomarkers, Fremont, Calif. All antibodies used for proteomics analysis were obtained from Cell Signaling (Beverly, Mass.), Upstate Biotechnology (Lake Placid, N.Y.), Neomarkers (Fremont, Calif.) and Santa Cruz (Santa Cruz, Calif.) (Table 2). Referring to Table 2, Abs designated as "mouse" were monoclonal Abs, and Abs designated as "rabbit" were polyclonal Abs. The ECL detection reagent was obtained from Amersham (Arlington Heights, Ill.).

Evaluation of Cellular Proliferation by Crystal Violet Assay

One×$10^3$ cells per well were seeded in 96 well dishes (Corning Costar, Cambridge, Mass.). Primary cultures of HMECs, A1N4 and 184B5 cells were evaluated at two different cell densities (seeded at 1×$10^3$ and 2×$10^3$ per well). After 24 hours of cell attachment, cells in triplicate wells were treated with pentamer at a concentration of 100 µg/mL. The cells on the same plate were treated with corresponding controls: (i) media containing DMSO, and (ii) media with no additions.

Cells were treated for 1, 2, 3, 6, 8 and 10 days, but in some cases, the samples were collected at days 2, 3, 4, 7 and 10 post-treatment. Each treatment was conducted in triplicate. Samples were collected at each time point as follows: media was removed and 50 µL of crystal violet solution (0.1% of crystal violet in 0.1 M citric acid solution) was added to each well at room temperature and plates were incubated for 15 minutes, followed by washing with deionized water. Plates were dried at room temperature overnight. The following day, plates were destained by adding 100 µL of 0.1 M sodium citrate solution into each well. Plates were incubated for one hour. The optical density (OD) of samples was read at 550 nm on an Ultramark Microplate Imagining System (BioRad, Philadelphia, Pa.). The experiment was repeated twice resulting in an average of nine measurements per sample. Statistical significance was determined using the t test analysis.

Mitochondrial Membrane Potential

Mitochondrial membrane potential was determined using ApoAlert™ Mitochondrial Membrane Sensor Kit (Clonetech Inc., Palo Alto, Calif.). The MDA MB-231, MCF-7, MDA MB-468, MDA MB-436, SKBR-3, MCF-10A, MCF-10A-c-Myc and AIN4 cells were grown, in appropriate media, to 60-70% confluence in 25 $cm^2$ dishes. The following day, the complete media was replaced with complete media containing (i) pentamer (100 µg/mL, or in some cases with 25 µg/mL), (ii) media with DMSO, or (iii) media only. Initially, cells were grown in the presence of pentamer for 1, 2, 3, 6, 12 and 24 hrs but only 1, 2 and 6 hrs treatments were selected for subsequent studies. All floating and adherent cells were combined, and then the cells were aliquoted into flow cytometry tubes. Approximately, $1 \times 10^6$ cells per tube were analyzed, according to the manufacturer's instructions. Samples were analyzed at the Lombardi Comprehensive Cancer Center Core Flow Cytometry Shared Resource Facility.

Layered Protein Scanning of Liquid Samples in Multi-well Plate (LPS/MWP)

Layered Protein Scanning (LPS) is a method for screening liquid protein samples in a high throughput manner using multi-well plates [Englert, C. R. et al., Cancer Res., 60: 1526-1530, 2000], and conducted by 20/20 Gene Systems, Inc., (Rockville, Md.). In short, cells are lysed and protein extract loaded into the wells of vacuum manifold and transferred through a stack of membranes. From each set of samples, up to five dot blot membranes are generated.

MDA MB-231 human breast cancer cells were treated, with or without 100 μg/mL pentamer, for 48 and 72 hours. Cells were lysed in LPS/MWP lysis buffer (20/20 Gene Systems, Inc.). Protein concentration was determined using BCA Protein Assay Kit (Pierce, Rockford, Ill.). Ten and 20 μg of each protein sample was loaded in duplicate onto Bio-Dot Microfiltration Apparatus (BioRad, Philadelphia, Pa.) and transferred through a 5-membrane stack as recommended by the manufacturer (20/20 Gene Systems). After the transfer, all of the membranes were biotinylated in 1 mg/mL EZ-Link Sulfo-NHS-Biotin solution in 1×PBS for 10 minutes at room temperature (Pierce).

Membranes were incubated overnight at 4° C. with the antibodies shown in Table 1 (1:500 or 1:1000 dilution). The following day, membranes were washed in Tris-buffered saline with Tween 20 (0.1%) (TBST buffer) and incubated for 60 minutes at room temperature in a mixture of FluoroLink Cy 5-labeled Streptavidin (1:500, Amersham) and Fluorescein-labeled secondary anti-mouse or anti-rabbit antibody (1:2,000, Molecular Probes, Eugene, Oreg.), followed by washes in TBST. Membranes were dried and scanned on a Typhoon scanner (Amersham), and obtained images were analyzed with InageQuant software (Amersham). Data were plotted in Excel and statistically analyzed in JMP (SAS Institute, Inc., Cary, N.C.). Hierarchical clustering analysis was performed to evaluate segregation of samples into control and treated groups.

TABLE 2

Antibodies used in LPS-multi well plate analyses

| MEMBRANE | PROTEIN/AB | 2 AB | DILUTION |
|---|---|---|---|
| 1A | Cleaved Caspase 3 (Asp175) | Rabbit | 1:500 |
| 1B | Cleaved Caspase 7 (Asp198) | Rabbit | 1:500 |
| 1C | Cleaved PARP | Rabbit | 1:500 |
| 1D | Cleaved Caspase 9 (Asp330) | Rabbit | 1:500 |
| 1E | p38-MAPK-P | Rabbit | 1:500 |
| 1F | 44/42-MAPK-P | Rabbit | 1:500 |
| 1G | SAPK/JNK-P | Rabbit | 1:500 |
| 1H | pRb MIX--pRb Ser795 + pRb Ser 807/811 | Rabbit | 1:1000 each |
| 2A | CHK2-P | Rabbit | 1:500 |
| 2B | CHK1-P | Rabbit | 1:500 |
| 2C | Cdc2-P (Tyr15) | Rabbit | 1:500 |
| 2D | p53-P | Rabbit | 1:500 |
| 2E | Stat-P (MIX)-Stat3-Tyr701 +Stat3-Ser727 | Rabbit | 1:1000 each |
| 2F | Stat3-P | Rabbit | 1:500 |
| 2G | Stat1-P | Rabbit | 1:500 |
| 2H | Stat6-P | Rabbit | 1:500 |

TABLE 2-continued

Antibodies used in LPS-multi well plate analyses

| MEMBRANE | PROTEIN/AB | 2 AB | DILUTION |
|---|---|---|---|
| 3A | PTEN-P (Ser380) | Rabbit | 1:500 |
| 3B | AKT-P (Mix of Ser473/Thr308) | Rabbit | 1:1000 each |
| 3C | AKT-total | Rabbit | 1:500 |
| 3D | PDK1-P (Ser241) | Rabbit | 1:500 |
| 3E | GSK3-β-P | Rabbit | 1:500 |
| 3F | FKHR-P (Ser256) | Rabbit | 1:500 |
| 3G | PKD/PKC-SER744/748 | Rabbit | 1:500 |
| 3H | PKC/PKC M Ser916 | Rabbit | 1:500 |
| 4A | PKC-δ (Ser 643) | Rabbit | 1:500 |
| 4B | PKC α/β II-P | Rabbit | 1:500 |
| 4C | PKC-PAN-P | Rabbit | 1:500 |
| 4D | PKC- ζ/λ-P | Rabbit | 1:500 |
| 4E | PKC-θ-P | Rabbit | 1:500 |
| 4F | PKC δ-P (Thr 505) | Rabbit | 1:500 |
| 4G | P53-P Cocktail 1 (Ser6, Ser9 and Ser20) | Rabbit | 1:1000 each |
| 4H | P53-P Cocktail 2 (Ser37, Ser46 and Ser392) | Rabbit | 1:1000 each |
| 5A | EGFR | Mouse | 1:500 |
| 5B | 44/42-MAPK-total | Rabbit | 1:500 |
| 5C | EGFR-P (Tyr1173) | Mouse | 1:500 |
| 5D | Bcl-X1 | Rabbit | 1:500 |
| 5E | mTOR-P (Ser 2448) | Rabbit | 1:500 |
| 5F | Bcl-2 | Mouse | 1:500 |
| 5G | Mouse IgG | Mouse | |
| 5H | Rabbit IgG | Rabbit | |

Confirmation of LPS/MWP Results by Immunoblotting

The proteins affected by pentamer, as detected by LPS, were analyzed further by immunoblotting. Antibodies against the following proteins were used: Cdc2 (Tyr15), FKHR (Ser256), p53 (Ser37, Ser46 and Ser392), PKC-δ (Ser643), PKC-θ (Ser643/676), pRb (Ser795 and Ser807/811), SAPK/JNK (Thr183/Tyr185) and Stat 5 (Tyr694) (all antibodies were obtained from Cell Signaling).

Protein pellets from pentamer-treated MDA MB-231, MDA MB-468 and MCF-7 cells and corresponding DMSO-treated controls were lysed in PBS with 1% SDS and sonicated for 15 seconds at a power of five watts. Samples were then centrifuged at 10,000 rpm and supernatants transferred into clean tubes. Protein concentration was determined as descried above. Ten jig of each protein sample was separated by PAGE on 4-20% gradient gels (BioRad, Philadelphia, Pa.). Gels were either transferred to PVDF membranes (BioRad) or P-FILM membrane (stacks of 10 membranes) according to the manufacturer's instructions (20/20 Gene Systems). PVDF membranes were blocked for 1 hour in 0.5% casein solution (Vector Laboratories, Burlingame, Calif.), prior to incubation with primary antibodies. P-FILM membranes do not require blocking prior to incubation with primary antibodies. The membranes were incubated overnight at 4° C. in 1:500 dilutions of primary antibodies, washed three times in TBST for five minutes, incubated in HRP-conjugated secondary antibodies, washed again and incubated in ECL Plus Reagent (Amersham). Signals were visualized on BIOMAX MR film (Kodak, Rochester, N.Y.). Following incubation with primary antibodies, membranes were incubated in anti-GAPDH antibody (1:500 dilution; Chemicon, Temecula, Calif.). The presence of this protein was visualized with secondary antibody conjugated to alkaline phosphatase DuoLux substrate (Vector Laboratories).

As a control, the PVDF membranes probed for Cdc2, FKHR, p53, and pRb were stripped according to manufacturer's instructions (Cell Signaling). After striping, membranes were washed four times for five minutes each in TBST buffer, blocked as described above, washed again and incubated in primary antibodies overnight at 4° C. The primary antibodies used were anti-total Cdc2 (1:1000 dilution, Cell Signaling), anti-total FKHR (1:1000 dilution, Cell Signaling), anti-endogenous p53 (1:1000, Cell Signaling) and anti-endogenous pRb (1:1000, Santa Cruz). The next day, membranes were washed and incubated in HRP conjugated secondary antibodies, washed again and incubated in ECL Plus Reagent (Amersham). Signals were detected as previously described. To test equality of loading, membranes were probed with anti-GAPDH antibody (1:500 dilution; Chemicon, Temecula, Calif.) as described above.

High Resolution Profiling of p53 and pRb

Both p53 and pRb contain multiple phosphorylation sites, and evaluating each site separately provides a more accurate indication of each protein's potential function. Therefore, a high resolution functional profiling of the proteins was performed using P-FILM technology (20/20 Gene Systems, Inc.).

The same protein samples as those used for PDVF membrane blotting were used. Ten µg of each protein sample of MDA MB-231 cells, and in some cases MDA MB-468 and MCF-7 cells, treated with 100 µg /mL of pentamer or DMSO-treated controls, were separated by PAGE on 4-20% gradient gels (BioRad). Proteins were transferred on a stack of ten membranes, according to manufacturer's instructions (20/20 Gene Systems, Inc.). The membranes were probed with antibodies recognizing total and phosphorylated p53 (p53Ser6, Ser9, Ser15, Ser20, Ser37, Ser46 and Ser392) at 1:1000 dilution as recommended by the manufacturer (Cell Signaling). The secondary antibody used in all cases was anti-rabbit polyclonal 1:2000 (Amersham). Signals were visualized on BIOMAX MR film (Kodak). The profiling of pRb was done using anti-phospho pRb (Ser780, Ser 795 and Ser 807/811) and anti-pRb polyclonal antibody (Cell Signaling) at a 1:1000 dilution. The secondary antibody used in all cases was anti-rabbit at 1:2000 dilution (Amersham). Image analysis was performed with Kodak 1D image analysis software. Background corrected intensity values were normalized for loading by using GAPDH intensities. Numerical analysis was performed in Excel.

RESULTS

Pentamer-induced Growth Inhibition

Human breast cancer cell MDA MB-231, MDA MB-436, SKBR-3, and MDA MB-468 cells were more sensitive to pentamer-induced growth inhibition than non-transformed, spontaneously immortalized, human mammary epithelial MCF-10A cells (which were resistant to pentamer). Ten days after pentamer treatment, the growth of MDA MB-231, MDA MB-436, SKBR-3, and MDA MB-468 cells was inhibited 5-fold; 4.1-fold; 5.5-fold and 4-fold, respectively, in comparison to DMSO-treated controls. Similarly to MCF-10A cells, normal mortal HMECs were refractory to growth inhibitory effects of pentamer, being inhibited only 1.4-fold. The benzo(a)pyrene-immortalized, non-transformed 184B5 and AIN4 cells were 2.8-fold and 7.3-fold growth inhibited, respectively, in comparison to DMSO-treated controls. Most of the breast cancer cells exhibited significant sensitivity to pentamer at day 6 post-pentamer treatment, earlier than immortalized 184B5 cells, which exhibited significant sensitivity to pentamer at day 10 post-treatment.

The growth inhibitory effects of pentamer on the above tumor cells is independent of p53 and ER status since the pentamer treatment also caused significant, 5.6-fold, growth inhibition of MCF-7 cells, which contain wild type p53 and are ER-positive. Also, the effect of pentamer is independent of the cell proliferation rate since both slow-proliferating MCF-10A cells (population doubling time 31.4 hrs ), and high-proliferating MCF-10A-c-Myc (population doubling time 20.4 hrs) and MCF-10A-ErbB2/Ras (four-fold more rapid doubling time compared to parental MCF-10A cells) were equally resistant to pentamer-induced growth inhibition.

Pentamer-Induced Depolarization of Mitochondrial Membrane Potential

Most transformed breast cancer cells exhibited high depolarization of the mitochondrial membrane, following treatment with pentamer (Table 3, representing average data from three experiments). The exception to this observation was MCF-7, where after several attempts using different passages, depolarization could not be demonstrated.

TABLE 3

| Cell Line | MMP depolarization (%) | | |
|---|---|---|---|
| | DMSO | Pentamer | Fold Increase |
| AIN4* | 6.34 | 20 | 3.2 |
| MCF-10A* | 10 | 20 | 2 |
| MDA MB-231 | 4 | 58 | 14.5 |
| MDA MB-468 | 12 | 60 | 5 |
| MDA MB-436 | 8.8 | 50 | 5.7 |
| SKBR-3 | 10 | 25 | 2.5 |

*Immortalized cell lines

MDA MB-231 cells exhibited a high degree of mitochondrial membrane depolarization (an average 58%) in response to pentamer, while depolarization of membranes in DMSO-treated cells ranged from 5 to 10%. However, pentamer treatment resulted in depolarization of the mitochondrial membrane in only 20% of the MCF-10A cells. DMSO treatment caused depolarization of the mitochondrial membrane in only 10% MCF-10A. These results were within the expected background values. Similar results were obtained when cells were treated with media only. In addition, similar resistance to membrane depolarization in pentamer-treated MCF-10A-Myc cells was detected. In MDA MB-436, MDA MB-468 and SKBR-3 cells, pentamer also caused significant depolarization of the mitochondrial membrane (Table 3).

In another experiment, MCF-10A and MDA MB-231 were cells were exposed to pentamer for 1, 2 and 6 hours. The results showed that 100 µg/mL of pentamer caused a time-dependent depolarization of mitochondrial membrane only in MDA MB-231 cells Similarly, only MDA MB-231 cells exhibited a dose-dependent response to 25 and 100 µg/mL of pentamer.

Pentamer-Induced Decrease in PARP Expression.

To determine whether depolarization of the mitochondrial membrane, induced by pentamer leads to apoptotic cellular death in human breast cancer cells lines, MDA MB-231 and MCF-7 cells were examined for PARP cleavage products. Since PARP is one of the downstream substrates of the caspase cascade, it is an excellent marker of apoptosis [Soldani, C. et al., *Apoptosis,* 7: 321-328, 2002].

The results indicated the main band of PARP to remain uncleaved in MDA MB-231 cells after 48 hours treatment with pentamer, and provided no evidence for the expected 85 kDa cleavage product. An unidentified protein band below the 116 kDa molecular weight position for PARP was observed in all untreated controls, but was absent from pentamer-treated cells. The significance of this band is not known at this time.

In MCF-7 cells, which lack caspase 3, treatment with pentamer for 48 hours, caused decrease in full-length PARP (116 kDa). This result could be due to the action of either caspase 7 or 6 in these cells. However, no cleaved PARP fragment was detected. Currently, the role of pentamer in induction of apoptosis in human breast cancer cells is being further investigated.

Pentamer Targets in Breast Cancer Cells

The proteins selected as potential pentamer targets for LPS screening were those commonly involved in the control of cellular growth, proliferation, survival and apoptosis (see Table 1). A total of 45 different antibodies were used in the screening with an emphasis placed on the phosphorylation status of tested proteins, indicating their active status.

The LPS test results indicated that the phosphorylation status of eight proteins was affected by pentamer: Cdc2, FKHR, p53, PKC-δ, PKC-θ, pRb, SAPK/JNK and Stat 5. Phosphorylation of five proteins was decreased by pentamer within 48 hrs, while phosphorylation was decreased in all eight proteins after 72 hrs of pentamer treatment.

In comparison with respective controls, and based on densitometry, phosphorylation of Cdc2 (Tyr15) decreased 31% after 48 hrs, and 45% after 72 hrs of treatment, phosphorylation of FKHR (Ser256) decreased 63% after 72 hours; phosphorylation of p53 (as detected with antibody mix at Ser37, 46 and 392) decreased 36% post treatment; phosphorylation of PKC-δ at Ser643 decreased 22% at 48 hrs and 49% after 72 hrs; phosphorylation of PKC-θ at Ser 643/676 decreased by 49% only after 72 hrs; phosphorylation of pRb at Ser 795 and Ser807/811 decreased by 36% at 48 hrs and 40% by 72 hrs post treatment; phosphorylation of SAPK/JNK at Thr183/Tyr185 decreased 34% at 48 hrs and 26% at 72 hrs post treatment; and Stat 5 phosphorylation at Tyr 694 decreased by 28% at 48 hrs and by 33% at 72 hrs. Protein p53 residues Ser6, Ser9, Ser20 and Ser15 were not significantly affected by pentamer. Although the phosphorylation of these proteins was affected by pentamer, their total cellular protein expression was not affected. Statistical analyses showed clustering based on the behavior of proteins listed in all samples analyzed by LPS after 72 hours of pentamer treatment. Analysis showed clear segregation between control and treated groups.

The results of the LPS analysis for Cdc2-P, FKHR-P, p53-P and pRb are represented in FIG. 1A.

Referring to FIG. 1B, immunoblotting was used to confirm the LPS results. In this assay, pentamer had an effect on phosporylated forms of Cdc2 (Tyr15) at both 48 and 72 hrs, FKHR (Ser256) 48 and 72 hrs, p53 (Ser37, Ser46 and Ser392) at 72 hrs, and pRb (Ser795 and Ser807/811) at 48 and 72 hr.

Total protein expression of Cdc2, FKHR and p53 was not affected by pentamer as evidenced by LPS analysis (FIG. 1A), and from PVDF membrane experiments. However, with respect to pRb, both total and phospho-specific sites were affected by pentamer (FIG. 1C). Equal loading was confirmed by GAPDH expression (FIGS. 1B and 1C).

Using current experimental immunoblotting conditions and PVDF membranes the results obtained by LPS initial screening on pentamer's effects on: PKC-δ, PKC-θ, SAPK/JNK and Stat5 were not confirmed.

Pentamer Decreases Phosphorylation of p53 (Ser392) and pRb (Ser780, Ser795 and Ser807/811)

Figure 2:
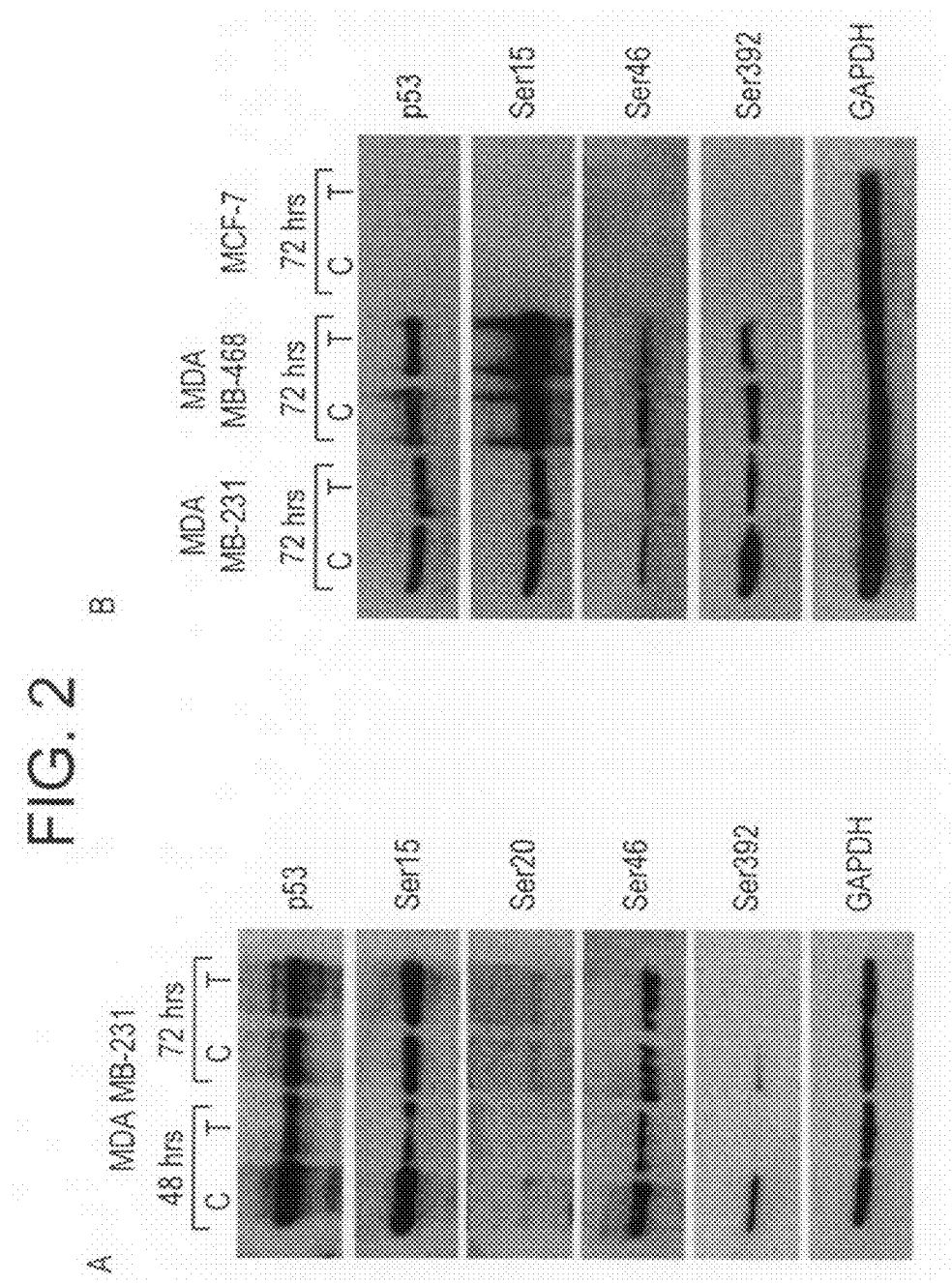
FIG. 2A-B represents high resolution profiling of p53 in human breast cancer cells treated with pentamer. A) LPS immunoblot of MDA-MB-231 cells treated with pentamer for 48 and 72 hrs and corresponding DMSO-treated controls; B) LPS immunoblot of MDA MB-231, MDA MB-468 and MCF-7 cells treated with pentamer and DMSO for 72 hrs in a separate experiment from A). To test for equality of loading, blots were probed with GAPDH. The data are representative of two independent immunoblotting analysis using same protein samples.

Both p53 and Rb contain a number of phosphorylation sites, and each separate site determines specific protein function. Because of the effects of pentamer on $G_0/G_1$ cell cycle growth arrest where both p53 and pRb play a crucial role in controlling this phase of the cell cycle, high resolution functional profiling of these two proteins in MDA MB-231 treated with 100 μg/mL of pentamer for 48 and 72 hrs and corresponding DMSO-treated controls using P-FILM technology (20/20 Gene Systems) was performed. Results of this analysis are shown in FIGS. 2 and 3.

As shown in FIG. 2A, the levels of endogenous p53 expression in MDA MB-231 cells were slightly decreased in pentamer-treated samples only after 48 hrs. Based on densitometry data this decrease was not significant (data not shown). Profiling the serine residues of p53 revealed only slight decreases in phosporylation of Ser15 residue and Ser46 at 48 h post treatment (FIGS. 2A and 2B), while significant dephosphorylation of p53 Ser392 residue was detected in response to pentamer at both 48 and 72 hrs post-treatment (FIG. 2A). Additional confirmation of the results was obtained by traditional immunoblotting on PVDF membrane. Phosphorylation of the Ser20 residue was decreased at 48 hrs, but was not affected in samples treated with pentamer for 72 hrs (FIG. 2A). The comparability of protein loading was confirmed by monitoring GAPDH protein expression (FIG. 2A).

In addition to MBA MD-231 cells, p53 status was evaluated in MDA MB-468 (mutated p53) and MCF-7 (wild type p53) treated with pentamer at 48 and 72 hrs treatment periods. Similarly to MDA MB-231 cells, expression of endogenous p53 in MDA MB-468 was not significantly affected by pentamer treatment (FIG. 2B). When compared, the percentage of p53 phosphorylated at Ser392 was decreased in both MDA MB-231 (53% compared to untreated controls) and MD MB-468 cells (33% compared to untreated controls), while Ser15 and Ser46 were not significantly affected in MDA MB-468 cells.

Under the same experimental conditions, no signal was detected for endogenous wild type p53 or phosphorylated p53 in MCF-7 cells (FIG. 2B). This result was expected because endogenous levels of wild type p53 are not easily detected by immunoblotting, in contrast to mutated p53, which is overexpressed (DiCioccio et al., *Cancer Genet Cytogenet.*, 105: 93-102, 1998).

Referring to FIG. 3, the phosphorylation status of pRb at Ser780, Ser795 and Ser807/811 in MDA MB-231 cells in response to pentamer was also studied. Pentamer treatment caused a decrease in protein expression of endogenous pRb, possibly resulting in the decrease of phosphorylation on all tested residues at 48 and 72 hours post treatment. Based on GAPDH protein expression, the samples were loaded equally.

What is claimed is:

1. A method of inducing dephosphorylation of a hyperphosphorylated cell cycle regulatory protein in a tumor cell in which hyperphosphorylation of said protein contributed to transformation, comprising contacting the tumor cell in need thereof with an effective amount of a compound having the formula $A_n$, or a pharmaceutically acceptable salt thereof:

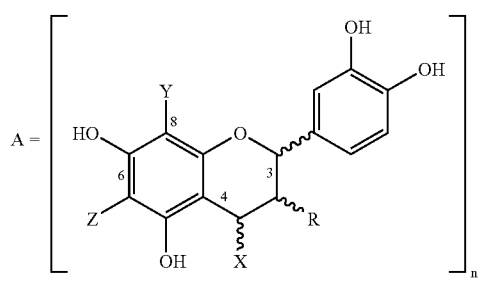

wherein n is 5;

R and X each have either α or β stereochemistry;

R is OH;

the substituents of C-4, C-6 and C-8 are X, Z and Y, respectively, and bonding of monomeric units occurs via C-4→C-8 linkage, and;

when any C-4, C-6 or C-8 is not bonded to another monomeric unit, X, Y and Z are hydrogen.

2. The method of claim 1, wherein the cell cycle regulatory protein is selected from the group consisting of Cdc2, forkhead transcription factor (FKHR), p53 and retinoblastoma protein (pRb).

3. The method of claim 2, wherein the compound has the following formula:

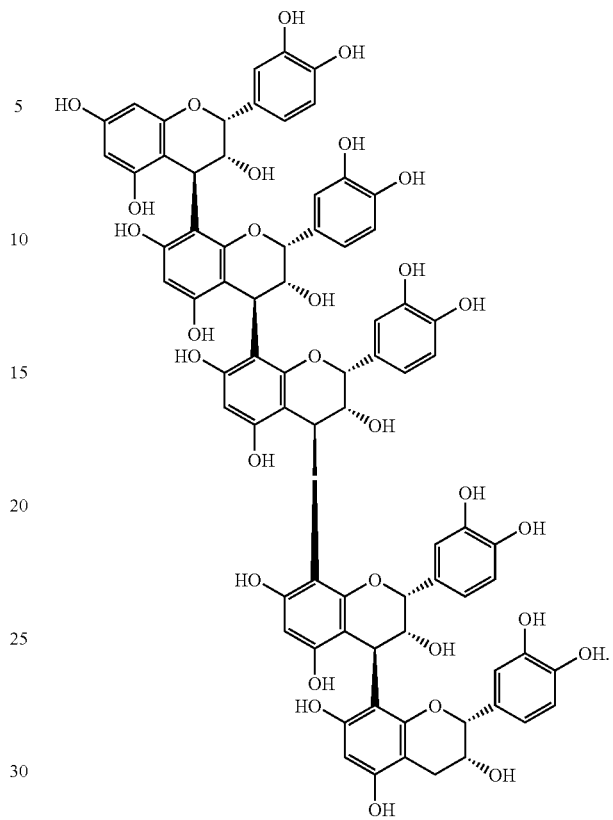

5. The method of claim 1, wherein the tumor cell overexpresses p53, and said p53 is hyperphosphorylated at at least amino acid position Ser392.

6. The method of claim 5, wherein the compound has the following formula:

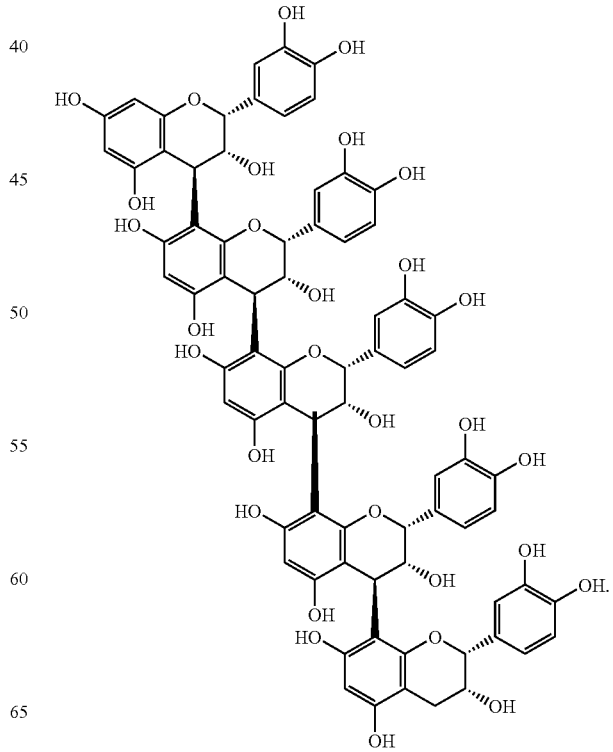

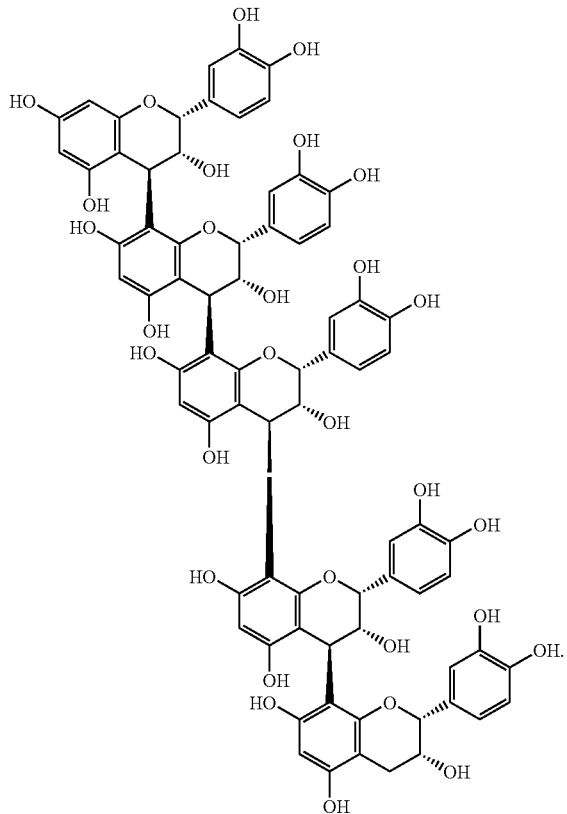

4. The method of claim 1, wherein the compound has the following formula:

7. The method of claim 1, wherein the tumor cell overexpresses AKT kinase.
8. The method of claim 7, wherein the compound has the following formula:
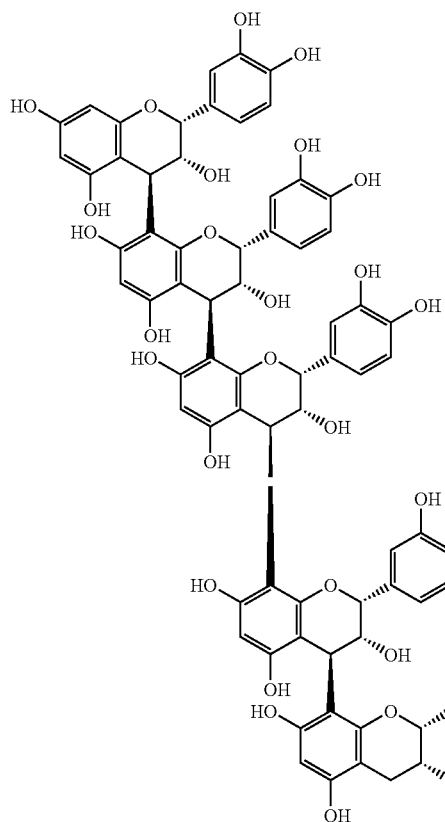
9. The method of claim 1, wherein the tumor cell overexpresses cyclin D1.
10. The method of claim 9, wherein the compound has the following formula:
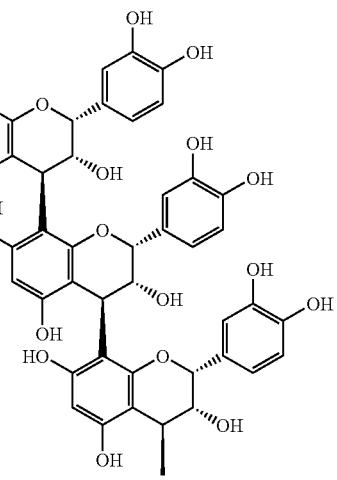
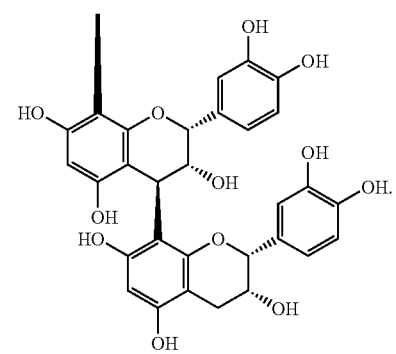
* * * * *